United States Patent
John et al.

(10) Patent No.: US 7,169,759 B1
(45) Date of Patent: Jan. 30, 2007

(54) TETRAPEPTIDE INHIBITORS OF β-SECRETASE

(75) Inventors: Varghese John, San Francisco, CA (US); Jay Tung, Belmont, CA (US); Lawrence Fang, Foster City, CA (US); Shumeye S. Mamo, Oakland, CA (US)

(73) Assignee: Elan Pharmaceuticals, Inc., So. San Francisco, CA (US)

( * ) Notice: Subject to any disclaimer, the term of this patent is extended or adjusted under 35 U.S.C. 154(b) by 336 days.

(21) Appl. No.: 09/594,667

(22) Filed: Jun. 15, 2000

Related U.S. Application Data

(60) Provisional application No. 60/139,173, filed on Jun. 15, 1999.

(51) Int. Cl.
  *A61K 38/00* (2006.01)

(52) U.S. Cl. .................. 514/18; 530/387.9; 530/388.1; 530/388.26; 530/389.1; 530/389.2

(58) Field of Classification Search .................. 514/18; 530/387.9, 388.1, 388.26, 389.1, 389.2
  See application file for complete search history.

(56) References Cited

U.S. PATENT DOCUMENTS

| | | | |
|---|---|---|---|
| 4,397,786 A | | 8/1983 | Evans et al. |
| 4,522,811 A | | 6/1985 | Eppstien et al. |
| 4,636,491 A | * | 1/1987 | Bock et al. .................... 514/16 |
| 6,627,739 B1 | * | 9/2003 | Anderson ................ 530/387.9 |

OTHER PUBLICATIONS

Bock, Mark G., et al. "Renin Inhibitors Containing Hydrophilic Groups. Tetrapeptides with Enhanced Aqueous Solubility and Nanomolar Potency" *J. Med. Chem..*, 31:1918-1923, 1988.
Agarwal, Nirankar S., et al. "Inhibition of Cathepsin D by Substrate Analogues Containing Statine and by Analogues of Pepstatin" *J. Med. Chem.*, 29:2519-2524.
Bringmann, G., et al. "Enantiomerically Pure N-Boc Protected β-Keto-γ-Amino Acid Esters form Simple Keto PrecursorsL A Novel, Sterocontrolled Approach to Statine Derivatives with Any Desired Configuration" *Synlett*, 5:253-255, 1990.
Cintas, P., "Asymmetric synthesis of α-amino acids from carbohydrates as chiral templates." *Tetrahedron*, 47(32):6079-6111, 1991.
Fieser, Mary, et al., *Reagents for Org. Syn.*, 4:418, 1974.
Freifelder, Morris, et al., "Low-pressure Hydrogenation of Alkozyanilines with Nobel Metal Catalysts" *J. Org. Chem.*, 30:2485-6, 1965.
Kessler, Horst, et al., "Short and Efficient Synthesis of Statine and Isostatine Derivatives" *Synthesis*, 6:457-458, 1990.
Korotzer, Andrew, et al. "Differential regulation by beta-amyloid peptides of intracellular free Ca2+ concentration in cultured rat microglia." *Eur. J. Pharmacol*, 288(2):125-130, 1995.
Kowall, Neil, et al. "An *in vivo* model for the neurodegenerative effects of β amyloid and protection by substance" *Proc Natl Acad Sci USA*, 88(16):7247-7251, 1991.
Lehninger, A.L., *Biochemistry: The Molecular Basis of Cell Structure and Function*, Chapter 4, Worth Publishers, NY, pp. 71-94, 1975.
Nishi, Takahide, et al., "The Practical Synthesis of N-Protected Allylamine: The Isoxazoline Route to Statine Analogue" *Heterocycles*, 29(9):1835-1842, 1989.
Precigoux, G. et al. "X-ray crystallography of linear peptides through renin-angiotesin system." *Peptides Biol. Fluids*, 35:476-476 (abstract), 1987.
Rich, Daniel, "Pepstatine-Derived Inhibitors of Aspartic Proteinases. A Close Look at an Apparent Transition-State Analogue Inhibitor" *J. Med. Chem.*, 28(3):263-273, 1985.
Sabbagh, M., et al. "β-Amyloid and Treatment Opportunities for Alzheimer's Disease." *Alz. Dis. Rev.*, 3:1-19, 1997.
Seubert, et al., "Isolation and quantification of soluble Alzheimer's β-peptide from biological fluids" *Nature*, 359:325-327, 1992.
Shiosaki, K. et al. "Potent and selective inhibitors of an aspartyl protease-like endothelin converting enzyme identified in rat lung." *J. Med. Chem.*, 36(4):468-478, 1993.
Paruszewski, R., et al., Enzymatically stable renin inhibitors containing statin and 6 aminohexanoic acid. Part IV *Boll. Chim. Farmaceutico*, 133(5):301-308, 1994.

\* cited by examiner

*Primary Examiner*—Bruce R. Campell
*Assistant Examiner*—Roy Teller
(74) *Attorney, Agent, or Firm*—McDonnell Boehnen Hulbert & Uerghoff LLP

(57) ABSTRACT

Statine-derived peptide inhibitors of the β-secretase enzyme are provided which are useful in the treatment of Alzheimer's disease and other diseases characterized by deposition of Aβ peptide in a mammal. The compounds of the invention provide useful methods of treatment by administration of these inhibitors to reduce Aβ peptide formation and pharmaceutical compositions.

111 Claims, No Drawings

TETRAPEPTIDE INHIBITORS OF β-SECRETASE

This application claims the benefit of U.S. Provisional Application No. 60/139,173, filed Jun. 15, 1999.

FIELD OF THE INVENTION

This invention is directed to compounds useful in treatment of Alzheimer's disease and more specifically to compounds that are capable of β-secretase enzyme inhibition, thus interfering with cleavage of amyloid precursor protein to produce beta-amyloid, a major component of the amyloid plaques found in the brains of Alzheimer's sufferers.

BACKGROUND OF THE INVENTION

Alzheimer's disease (AD) is a progressive degenerative disease of the brain primarily associated with aging which results in loss of memory and orientation. As the disease progresses, motor, sensory and linguistic abilities are also affected until there is global impairment of multiple cognitive functions of the brain. These cognitive losses occur gradually, but typically lead to severe impairment and eventual death in the range of four to twelve years.

Alzheimer's disease is characterized by two major pathologic observations in the brain: neurofibrillary tangles and amyloid (or neuritic) plaques. Neurofibrillary tangles occur not only in Alzheimer's disease but also in other dementia-inducing disorders, while amyloid plaques are peculiar to AD. Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

Neurofibrillary tangles are characterized as networks of microtubules and microfilaments which were once structural supports running symmetrically through the nerve cells that transported nutrients but have degenerated into dysfunctional tangled masses. They can be described histologically as non-membrane bound bundles containing paired, helically wound filaments (PHF) that are approximately 10 nm in length and located in the perinuclear cytoplasm of certain neurons. Major components of paired helical filaments are highly phosphorylated tau proteins (PHF-tau) of 60 kDa, 64 kDa and 68 kDa. Aβ peptide is also a component of these tangles. Tau belongs to the family of microtubule-associated proteins and plays a role in the microtubule assembly and stabilization. In certain other neurodegenerative disorders, including corticobasal degeneration (CBD), progressive supranuclear palsy (PSP) and Pick's disease, hyperphosphorylated tau proteins also accumulate in brain tissue in association with abnormal filaments. Recent research indicates that the pattern of hyperphosphorylation and the resulting ultrastructure of the helical filaments are somewhat different in each type of disease.

Amyloid plaques, on the other hand, are peculiar to and a defining feature of AD. Amyloid plaques are predominantly composed of amyloid beta peptide (Aβ, also sometimes designated as βA4). Aβ is derived by proteolysis of the amyloid precursor protein (APP) and is comprised of 39–43 amino acids. Several proteases called secretases are involved in the processing of APP. It appears that the abnormal processing and deposition of Aβ in areas of the brain responsible for cognitive activities is a major factor in the development of AD. Cleavage of APP at the N-terminus of the Aβ peptide by β-secretase and the C-terminus by one or more γ-secretases constitutes the amyloidogenic pathway, i.e., the pathway by which Aβ peptide is formed. Cleavage of APP by α-secretase and the same or a different gamma secretase produces α-sAPP, a secreted form of APP that does not result in amyloid plaque formation. This alternate pathway precludes the formation of AB. It has been proposed that Aβ peptide accumulates as a result of the processing of APP by β-secretase and that therefore inhibition of the activity of this enzyme is desirable for treatment of AD. See for example, β-*Amyloid and Treatment Opportunities for Alzheimer's Disease*, Sabbagh, M., et al., Alz. Dis. Rev. 3, 1–19, (1997).

Several lines of evidence indicate that progressive cerebral deposition of particular amyloidogenic proteins, β-amyloid proteins, (Aβ), play a seminal role in the pathogenesis of AD and can precede cognitive symptoms by years or decades. See, Selkoe, Neuron 6:487 (1991). Aβ is released from neuronal cells grown in culture and is present in cerebrospinal fluid (CSF) of both normal individuals and AD patients. See, Seubert et al., Nature 359:325–327 (1992).

Although diffuse deposition of Aβ peptide occurs in most all humans with aging, the formation of amyloid plaques occur only in AD patients. Formation of these plaques is believed to occur over a period of years or even decades. The Aβ peptide in amyloid plaques is always folded in a particular three-dimensional pattern called a beta-pleated sheet and appears to be chemically modified as well, which could explain the association of the Aβ peptides into the larger, denser plaques, rather than the diffuse deposits normally seen. Associated with this central core of Aβ peptide in the amyloid plaque are surrounding abnormal neurites and several types of altered glial cells. Glial cells normally associate with neurons and perform support and protective functions. On the outside of the plaque are reactive astrocytes, which are a type of glial cell typically found in injured brain areas. Additionally many other biochemical components, including enzymes, proteoglycans and apolipoproteins are present in the plaques. For a discussion of the formation of these plaques see for example: Sabbagh, M., et al., cited supra.

The neurons touching the amyloid plaques are progressively debilitated and ultimately die. At present it is not known whether the Aβ peptide is neurotoxic in itself or if the secondary features of the amyloid plaques, e.g., the abnormal glial cells, cause the nerve cells to die. Researchers have demonstrated that the Aβ peptide has neurotoxic effects in vitro. Still other researchers have demonstrated that the 25–35 amino acid sequence of Aβ peptide is similar to that of substance P, an endogenous neuropeptide compound present in certain brain tissues and having neuroexcitatory effects. Co-administration of substance P in the study blocked the neurotoxic effect of Aβ peptide in rats. See: *An in vivo model for the neurodegenerative effects of beta amyloid and protection by substance P.* Kowall N W, et al., Proc Natl Acad Sci USA 88 (16) p7247–51 (1991). Another study reports that Aβ peptide is neurotoxic through its interference with $Ca^{++}$ homeostasis. Korotzer A. R., et al., *Differential regulation by beta-amyloid peptides of intracellular free Ca2+ concentration in cultured rat microglia.* Eur. J. Pharmacol., 288 (2):125–30 1995. Further, some studies have proposed that Aβ peptide is responsible for the hyperphosphorylation of tau, a microtubule associated protein, which results in formation of PHFs and neurofibrillary tangles as described above. Thus, with Aβ peptide clearly linked to the formation of amyloid plaques and implicated in the formation of neurofibrillary tangles in AD, there is a need for agents and methods for reduction of Aβ peptide in vivo.

At present there are no published means for specifically inhibiting the β-secretase enzyme, or even structural identification of the β-secretase enzyme is or a peptide sequence of its active site. However, a commonly assigned application naming John Anderson, Guriqbal Basi, et al. as inventors and entitled: β-Secretase Enzyme Compositions and Methods, identifies the enzyme and methods of use thereof. Additionally, a commonly assigned application naming Varghese John, Jay Tung, Roy Hom and Larry Fang as inventors and entitled: Dipeptide Inhibitors of β-Secretase, describes and claims dipeptide inhibitors of the β-secretase enzyme. The two above-identified applications are being filed on the same day as the present application. The contents of these co-pending applications are hereby incorporated by reference in their entirety for all purposes. Additionally, U.S. Pat. No. 4,636,491 to Bock, et al. discloses certain tetrapeptides having renin inhibitory activity. Some of the compounds disclosed in the broadest Markush description by Bock encompass some of the compounds of the present invention. However, all the specific examples of Bock are directed to the sequence: Phe-His-Sta-Leu or to the same sequence containing derivatives of statine. The sequence is neither claimed, nor operative in the β-secretase inhibition disclosed herein. It is believed that the compounds claimed herein are patentable as a selected subgenus of the broad Markush disclosure of Bock.

DETAILED DESCRIPTION OF THE INVENTION

This invention is directed to the discovery of a class of compounds that inhibit β-amyloid peptide production by preferentially binding to and inhibiting the proteolytic function of the β-secretase enzyme. Inhibition of β-secretase enzyme stops or reduces the production of Aβ from APP and thus reduces or eliminates the formation of amyloid plaques and other types of Aβ deposition in the brain. Therefore, the compounds are useful in the prevention of Alzheimer's Disease in patients susceptible to AD and/or in the treatment of patients with AD in order to inhibit further deterioration in their condition. Now it has been discovered that the compounds of the present invention provide inhibitors of the β-secretase enzyme.

The invention relates to compounds of formula 1

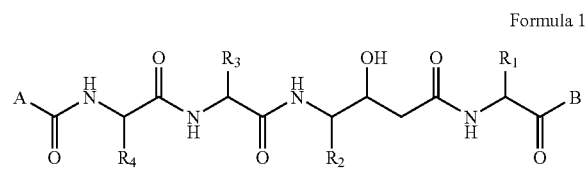

Formula 1 wherein

A is a straight or branched chain alkanoxy or alkenoxy of 1 to 5 carbon atoms, aryl, arylalkyl, the aryl being optionally substituted with 1 to 2 carbon atoms or halogen, adamantyloxy, or 4-aminobutanoic acid;

B is selected from the group consisting of hydroxy,

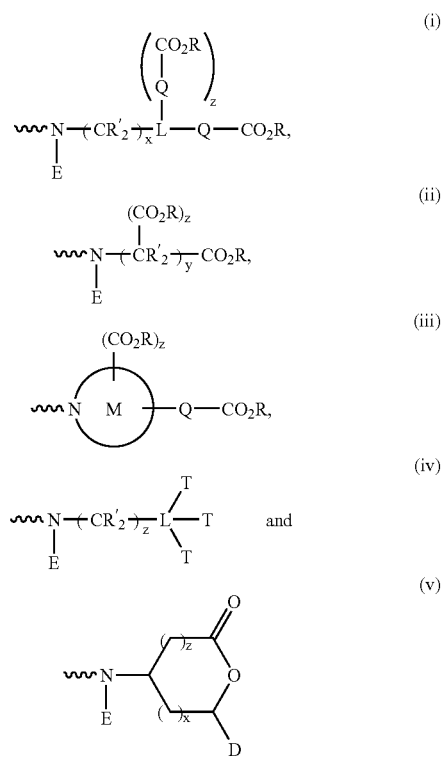

wherein a dithered line represents a point of attachment at B of formula 1;

D is H or an oxo group;

L is a 5 or 6 membered saturated, unsaturated or aromatic heterocycle having from 1 to 3 heteroatoms chosen from nitrogen, oxygen or sulfur, or a saturated, unsaturated or aromatic carbocycle of 3 to 6 carbon atoms, any group represented by L having optional substitution with R', OR', or halogen;

Q is a bond, or is a straight chain linking group of 1 to 3 non-hydrogen atoms chosen from the group consisting of —$CH_2$—, —O—, and —NH— wherein O and N may not be adjacent;

ring M is a stable 5 to 7-membered saturated, unsaturated or aromatic heterocycle having up to 2 additional N atoms and optionally having 1 to 2 atoms of O and S, T is independently selected from the group consisting of H, OH, $NO_2$, C(O)N(R)$_2$, F, $C_1$–$C_3$ alkoxy, hydroxymethyl and $CF_3$, wherein at least one T is other than H;

x is an integer of 1 to 3, y is an integer of 1 to 6, z is 0 (zero), 1 or 2,

R' is independently H, —OH, $C_1$–$C_2$ alkyl or phenyl,

R is independently H, $C_1$–$C_4$ alkyl, or phenyl, and E is H, or $C_1$–$C_2$ alkyl;

$R_1$ is $C_1$–$C_5$ alkyl;

$R_2$ is 2-propyl, 2-methylpropyl- or phenyl optionally substituted with R', OR' or halogen;

$R_3$ is phenyl, $C_1$–$C_5$ alkyl, or 1-(2-methylthio-)ethyl-;

$R_4$ is 2-propyl, 2-butyl or 2-methylpropyl; and stereoisomers, hydrates or pharmaceutically acceptable salts or esters thereof to reduce the formation of Aβ peptide.

Still further, it is an object of the present invention to provide pharmaceutical compositions containing such β-secretase inhibitors in a pharmaceutically acceptable carrier. Other objects of the invention will become apparent from reading the specification and appended claims.

Detailed Description of the Invention

Natural amino acids are available in abundance, and a great array of non-naturally occuring amino acids have been prepared by techniques well known to those skilled in the art of organic synthesis. Roberts and Vellaccio provide a comprehensive listing of non-natural amino acids, and techniques for the synthesis of many variations thereof in *The Peptides*, Vol. 5: Analysis, Synthesis, Biology; Academic Press, NY 1983. A more recent description of additional routes to chirally pure non-natural amino acids is in: *Asymmetric synthesis of α-amino acids from carbohydrates as chiral templates*; Cintas, P. Tetrahedron, 47 (32), 6079–111 (1991). Thus one skilled in the art can synthesize the amino acid precursors used in the preparation of the compounds of the invention by a judicious selection of one or more of the methods outlined above, which articles are hereby incorporated by reference.

Statine is a non-standard amino acid residue present in pepstatin that provides this peptide its inhibitory activity (Rich, D. H., *J. Med. Chem.* 28, p. 262 (1985). Interestingly, pepstatin has no inhibitory activity in assays with β-secretase. Statine has the chemical name (3S, 4S)-4-amino-3-hydroxy-6-methylheptanoic acid, and is further identified in the Merck Index ($11^{th}$ ed.) at monograph no. 8759, and is available commercially, such as through the Sigma-Aldrich catalog. The three letter abbreviation given to statine in the peptide art is Sta. The (3S, 4S) stereoisomer is designated Sta(s) or statine(s). Statine derivatives are also well known in the literature and can be prepared by methods disclosed in U.S. Pat. No. 4,397,786. Other methods are described in the series cited above (The Peptides, Vol. 5: Analysis, Synthesis, Biology; Academic Press, NY 1983] and by Bringmann et al. in Synlett (5), pp. 253–255 (1990); by Kessler and Schudok in Synthesis (6) pp. 457–8 (1990); and by Nishi and Morisawa in Heterocycles 29(9), 1835–42 (1989).

Unless defined otherwise, all scientific and technical terms used herein have the same meaning as commonly understood by one of skill in the art to which this invention belongs. All patents and publications referred to herein are hereby incorporated by reference in their entirety for all purposes.

Optical Isomers-Diastereomers-Geometric Isomers

Some of the compounds described herein contain one of more asymmetric centers and may thus give rise to enantiomers, diastereomers, and other stereoisometric forms which may be defined in terms of absolute stereochemistry as (R)- or (S)-, or as (D)- or (L)- for amino acids. The present invention is meant to include all such possible diastereomers and enantiomers as well as their racemic and optically pure forms. Optically active (R)- and (S), or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are intended to be included.

Stereoisomers refer to molecules wherein the same atoms attach to one other in the same order, but the positioning of the attachment varies so that two molecules may not be spatially identical; they are classified according to the number and symmetry of the chiral centers in each molecule. Chiral centers are atoms to which the same kinds of atoms are attached but have more than one possibility for arrangement around the chiral center atom. There are two types of stereoisomers: diastereomers and enantiomers.

Diastereomers are two molecules which are stereoisomers that have the same connectivity but are not mirror images of each other. Chiral centers in diastereomers are arranged so that an internal plane of symmetry exists in the molecule. The chemical and physical properties of diastereomers tend to differ because different spatial shape changes the ways in which the molecules interact.

Enantiomers are are two molecules which are exact mirror images of one other, because each chiral center is a reflection of the chiral center of the other enantiomer. Enantiomers have identical chemical and physical properties, which make separations based on their physical properties extremely difficult. Enantiomers are usually labeled R and S (for right-handed and left-handed) to distinguish them.

Racemic mixtures are defined as mixtures of two mirror image forms of the same molecule (enantiomers) in equal amounts.

Although stereoisomers may not vary greatly on a chemical level, on the biological level, different stereoisomers isomers "fit" differently into the various protein receptors that drive biochemical processes and thus stereoisomers, and frequently even enantiomers, do not bind equally. Therefore, enantiomers of the same compound can have different effects within the human body.

Many of the embodiments of the present invention embrace the residue—or side chain—of a naturally occurring α-amino acid, it is to be noted that each α-amino acid has a characteristic "R-group", the R-group being the residue—or side chain—attached to the α-carbon atom of the amino acid. For example, the residue of glycine is H, for alanine it is methyl, for valine it is 2-propyl, for methionine it is methylthioethyl. The specific residues of the naturally occurring α-amino acids are well known to those of skill in the art. See, e.g, A. L. Lehninger, Biochemistry: The Molecular Basis of Cell Structure and Function, 1975 (or any edition thereafter), Worth Publishers, NY, see, particularly Chapter 4). As used herein, the residues of naturally occurring α-amino acids are the residues of those about twenty α-amino acids found in nature which are incorporated into a protein by the specific recognition of the tRNA molecule with its cognate mRNA codon in humans.

Those non-naturally occurring α-amino acid residues embraced by the present invention are known to those of skill in the art. Statine, as discussed above in the background of the art is a commercially available γ-amino acid. In the compounds herein the preferred stereoisomer is the S configuration and the absolute stereochemistry is (3S, 4S).

Other modified or non-usual amino acids are 2-aminobutyric acid (Abu) and phenylglycine (Phg), In amino acids of this type a change is made in the side chain of the amino acid, usually by varying the length or substitution thereon. For instance, 2-aminobutyric acid is an α-amino acid that varies from valine by the removal of one of the methyl groups from the side chain. Phenylglycine is a homolog of the naturally-occurring amino acid phenylalanine, which lacks the methylene linkage between the peptide backbone and the phenyl group found in phenylalanine. Norleucine (Nle) is a slightly different example where the branching methyl group of leucine is shifted rather than deleted to make a non-branching (normal) chain having the same number of carbon atoms as leucine. These unusual amino acids can be incorporated into peptide chains using the standard peptide linkage synthetic procedures described below for the naturally-occurring amino acids.

As used herein, the term "alkyl" includes the straight, branched-chain and hydrocarbons, the number of carbons atoms being generally specified. Where not specified the alkyl groups preferably contain from about 1 up to about 12, more preferably 1 to 6, and most preferably 1 to 5 carbons. Exemplary of such moieties are methyl, ethyl, n-propyl, isopropyl, n-butyl, t-butyl, sec-butyl, pentyl, n-hexyl, n-nonyl, n-decyl, and the like. The term "lower alkyl" includes $C_1$–$C_5$ alkyl groups such as methyl, ethyl, n-propyl, isopropyl, n-butyl, s-butyl, t-butyl, n-pentyl, and the like.

As used herein, "heteroatom(s)" is/are selected from O, N or S, unless otherwise specified.

Alkenes are alkyl groups containing at least one C—C double bond (—C=C—). Exemplary of alkenyl moieties are 2-methyl-2-propenyl, 2-methyl-1-propenyl, propenyl, 1-butenyl, 2-butenyl, 3-butenyl, 2,2-difluoroethenyl, as well as those straight and branched chained moieties having more than one double bond.

The term "lower alkyl" includes $C_1$–$C_5$ alkyl groups such as methyl, ethyl, n-propyl, isopropyl, n-butyl, s-butyl, t-butyl, n-pentyl, and the like.

The term "halo" and "halogen" refer to chloro, bromo, fluoro, and iodo.

"Lower alkenyl" refers to those $C_2$–$C_6$ unsaturated groups such as vinyl, 1-propene-2-yl, 1-butene-4-yl, 1-pentene-5-yl, 2-methyl-2-butene-4-yl and the like.

The term "alkanoxy" refers to those groups having an alkyl moiety from 1 to 6 carbon atoms linked to an oxygen atom. This oxygen is linked to the carbon atom of another group. Examples of alkanoxy groups are: methoxy, ethoxy, propoxy, butoxy, iso-butoxy, and the like.

The term "alkenoxy" includes $C_2$–$C_6$ groups having a C—C double bond and an oxygen atom, such as ethenyloxy, propenyloxy, iso-butoxyethenyl and the like.

The term "amine" includes pirmary, secondary and tertiary amine which may be in straight or branched chains or, in the case of secondary and tertiary amines within rings, and are optionally substituted with, $C_1$–$C_7$ acyloxy, $C_1$–$C_6$ alkyl, $C_1$–$C_6$ alkoxy, nitro, carboxy, carbamoyl, carbanoyloxy, cyano halogen, amino and the like.

The terms "carboxyl", "carboxylate" and "carbamoyl" are all terms referring to functional groups containing the a carbon atom double bonded to an oxygen as well as single bonded to another oygen, in the case of carbamoyl the carbon is addionally bonded to a nitrogen atom. These terms all include the corresponding pharmaceutically acceptable $C_1$–$C_6$ alkyl and aryl esters.

The term "aryl" includes 3 to 8 membered stable saturated or unsaturated organic monocyclic rings having 0 to 4 hetero atoms selected from S, O, and N; and 7 to 10 membered organic stable, saturated or unsaturated, bicyclic rings having 0 to 5 hetero atoms selected from S, O, N; both of which may be substituted by halo, $C_1$–$C_6$ alkyl, $C_1$–$C_6$ alkoxy, $C_2$–$C_6$ alkenyl, $C_2$–$C_6$ alkynyl, substituted $C_1$–$C_6$ alkyl, $C_1$–$C_6$ substituted alkoxy, substituted $C_2$–$C_6$ alkenyl, or substituted $C_2$–$C_6$ alkynyl, hydroxy, amino, nitro, cyano, carboxy, hydroxymethyl, aminomethyl, carboxymethyl, $C_1$–$C_4$ alkylthio, $C_1$–$C_4$ alkanoyloxy, carbamoyl, or halo-substituted $C_1$–$C_6$ alkyl. The term "aryl" also includes fused ring carbocyclic and heterocyclic moieties having at least one aromatic nucleus. The term "arylalkyl" refers to any of the above aryl groups also having an alkyl radical though which the group connects to the larger structure. Preferred aryl and aralkyl moieties are phenyl, benzyl, phenethyl, 1- and 2-naphthyl, naphthylmethyl, 5-, 6-, 7-, and 8-quinolinyl, benzofuryl, indenyl, or indanyl, benzimidazolyl, indolyl, benzothiophenyl, indole-3-ethyl and 5-, 6-, 7-, and 8-tetrahydroisoquinoline. Other examples of such ring systems may be found in J. Fletcher, O. Dermer, R. Fox, Nomenclature of Organic Compounds, pp. 20–63 (1974), and in the Examples herein.

The terms substituted alkyl, substituted alkenyl, substituted alkynyl and substituted alkoxy are these radicals substituted with halogen, hydroxy, amino, $C_1$–$C_7$ acyloxy, nitro, carboxy, carbamoyl, carbamoyloxy, cyano, or $C_1$–$C_6$ alkoxy, and may be substituted one or more times with the same or a different group, preferably substituted 1 to 3 times.

A linking group is defined as a divalent linear chain facilitating the reach of a binding group, for example a carboxyl group to binding sites within the target enzyme. The facilitation occurs as a result of either or both the extension of the group at a particularly advantageous distance from another binding site on the molecule or in providing an advantageous flexibility to the group in being able to adopt a conformation that allows for optimal binding. Particular examples of the group Q which may be present in compounds of the invention include groups of formula: —CH$_2$—(CH$_2$)n-; —O—(CH$_2$)n-; NH—(CH$_2$)n-; —O—CH$_2$—O—; —O—CH$_2$—NH—; NH—CH$_2$—NH— wherein n=0, 1 or 2.

A pharmaceutically acceptable salt is any salt which substantially retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc. A pharmaceutically acceptable ester is any ester formed on a parent carboxylic acid which substantially retains the activity of the parent compound and does not impart any deleterious or undesirable effect on the subject to whom it is administered and in the context in which it is administered. A pharmaceutically acceptable excipient or diluent is any excipient which retains the activity of the therapeutic compound with which it is admixed and does not impart any deleterious or undesirable effect on the subject to whom it is administered and in the context in which it is administered.

Abbreviations used in this specification represent the following:

Ac=acetyl(methylcarbonyl)

bd=broad doublet

BOC=tert-butoxycarbonyl bs=broad singlet

CBZ=benzyloxycarbonyl d=doublet

DMF=dimthylformaide

EDC=ethyl-1-(3-dimethylaminopropyl)carbodiimide

EtOAc=ethyl acetate eq.=equivalents

HOBT=1-hydroxybenzotriazole

IC$_{50}$=inhibitory concentration of a compound where the enzyme activity is reduced by half.

m=multiplet mass. spec. or MS=mass spectrum nmr=nuclear magnetic resonance spectrum $R_f$=ratio of movement of a substance on a thin layer chromatogram in comparison to the movement of the solvent front.

s=singlet t=triplet

TEA=triethylacetate

TFA=trifluoroacetic acid

THF=tetrahydrofuran

TLC=thin layer chromatography

δ=units of measurement for nuclear magnetic resonance spectroscopy which are relative to a standard, e.g. trimethyl silane.

μL=microliter

μM=micromolar (an expression of concentration in micromoles/liter)

The terms N-terminal or N-terminus refer to that terminal or end group of a peptide bearing the free or derivatized amino group of an amino acid residue. Likewise, C-terminal or C-terminus refers to that terminal or end group of a peptide bearing the free or derivatized carboxy group of an amino acid residue. The term "capping group" refers to a non-amino acid moiety bonded to the C- or N-terminal of the peptide chain. Examples of N-terminal capping groups used in peptide synthesis are BOC (t-butoxycarbonyl,) and CBZ (benzyloxycarbonyl) and glutamic acid. Other capping groups are acetyl and adamantyloxycarbonyl. Non-limiting examples of are shown in Table 1.

Methods of Synthesis

Reaction scheme 1 illustrates the construction of some of the peptides provided herein and the variety of reactions that may be used to prepare intermediates from which compounds for formula 1 may be prepared, and provides a generic method for the synthesis of the tetrapeptides. Although statine and valine are employed as the N-terminal amino acids. It is to be understood that other peptides may be also be substituted in place of valine and that derivatives of statine may be employed as alternatives in the steps below to provide further tetrapeptides as provided herein.

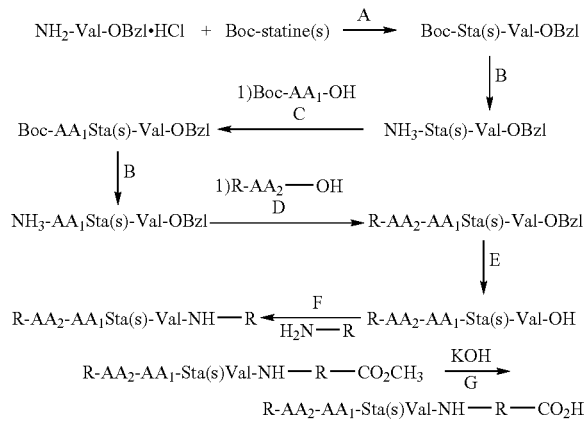

Scheme 1

This scheme may be varied as desired by selecting a different carboxy protected amino acid residue, for example, α-amino-butyric acid (Abu) or phenylglycine (Phg) in Step A to couple with statine. Or alternatively, selecting a different statine derivative, such as Phe-Sta, wherein the 2-methyl-propyl group is replaced by benzyl, to be coupled with the starting amino acid in Step A. Derivatives of statine are known in the art and described in U.S. Pat. No. 4,397,786.

Experimental Methods

Step A: Coupling of the C-Terminal Amino Acid with Statine.

Boc-Sta(s) (1.0 equiv.) was dissolved in 30 mL of dry dichloromethane, then HOBT (2.0 equiv.), H₂N-Val-OBzl-.HCl (1.0 equiv.) and TEA (5 equiv.) were added and the mixture was stirred for 20 minutes. EDC (1.2 equiv.) was then added and allowed to stir overnight under an atmosphere of nitrogen. The reaction was diluted with water and extracted with EtOAc (3×). The organic layers were washed with aqueous citric acid (2×), sat. NaHCO3 (2×), brine, then dried with MgSO₄.

Step B: Removal of the Boc-Protecting Group from the Resulting Dipeptide.

The Boc-protecting group of the dipeptide was dissolved in a trifluoroacetic acid/methylene chloride (1/1) solution. The reaction was monitored by TLC to confirm the consumption of starting material at which time the solvents were removed under vacuum to yield the free amine which was used without further purification.

Step C: Coupling Deprotected Amine with a Selected Amino Acid Residue (AA₁).

Boc-AA₁-OH (1.0 equiv.) is dissolved in 30 mL of dry dichloromethane, then HOBT (2.0 equiv.), H₂N-Stat-Val-OBzl.HCl (1.0 equiv.) and TEA (5 equiv.) were added and all was stirred for 20 minutes. EDC (1.2 equiv.) is added and the mixture is stirred overnight under an atmosphere of nitrogen. The reaction is then diluted with water and extracted with EtOAc (3×). The organic layers are washed with aqueous citric acid (2×), sat. NaHCO3 (2×), brine, then dried over MgSO₄.

Removal of the Boc-protecting group from the resulting tripeptide is accomplished as in Step B above.

Step D: Coupling of the Tripeptide with a Selected Amino Acid Residue (AA₂).

R-AA₂-OH (1.0 equiv.) is dissolved in 30 mL of dry dichloromethane, then HOBT (2.0 equiv.), H₂N-AA₁-Stat-Val-OBzl.HCl (1.0 equiv.) and TEA (5 equiv.) are added and the reaction mixture is stirred for 20 minutes. EDC (1.2 equiv.) is then added to the mixture and is allowed to stir overnight under an atmosphere of nitrogen. The reaction is diluted with water and extracted with EtOAc (3×). The organic layers are washed with aqueous citric acid (2×), sat. NaHCO3 (2×), brine, then dried over MgSO₄.

Step E: Removal of the Carboxybenzyl (Cbz) Protecting Group from the C-terminus

R-AA₂-AA₁-Stat-Val-OBz (1.2 g) is dissolved in 100 ml of MeOH and Pd/C (1 g, 10%) is added. The reaction is subjected to a hydrogen gas atmosphere of 50 psi for 2 hours. The resulting slurry is filtered through a pad of celite, and rotoevaporated to yield the desired material.

Step F: Coupling of the C-Terminal End of the Tetrapeptide with a Functionalized Amine R-AA₂-AA₁-Stat-Val-OH (1.0 equiv.) is dissolved in 30 mL of dry dichloromethane, then HOBT (2.0 equiv.), H₂N—R (1.0 equiv.) and TEA (5 equiv.) were added and the reaction mixture is stirred for 20 minutes. EDC (1.2 equiv.) is added and allowed to stir overnight under an atmosphere of nitrogen. The reaction is diluted with water and extracted with EtOAc (3x). The organic layers are washed with aqueous citric acid (2x), sat. NaHCO3 (2x), brine, then dried over MgSO$_4$.

The amine groups (R—NH2) of the examples shown below are commercially available unless otherwise indicated by reference to a citation in a journal. Some of the compounds are supplied as the methyl ester, if a carboxylic acid function is present. If only the free carboxylic acid group is available commercially, the methyl ester can be prepared as indicated in step H below.

Step G: Cleavage of the C-Terminal Capping Group Methyl Ester to Provide Free Carboxylic Acid or Carboxylate Salt The methyl ester (1 equiv.) is dissolved in a suitable solvent (MeOH/water, dioxane/water, or THF/water). Hydroxide (2–20 equiv., KOH, NaOH, or LiOH) is added and the reaction mixture is allowed to stir until the all of the ester is converted to acid as evidenced by TLC. Volatile solvents are removed and the reaction is acidified with citric acid. The resulting precipitate is collected and characterized to insure the desired material is obtained.

Step H: Preparation of the Methyl Ester for the C-Terminal Capping Reaction

The selected acid is dissolved in dry methanol. HCL (gas) is bubbled through the mixture for 5 minutes. The reaction is then stirred overnight and rotoevaporated to yield the desired methyl ester.

Step J: Aminoaryl Diesters to Aminocyclohexyl Diesters

An example of this ring hydrogenation is with dimethylaminophthalate. The aminophthalate in acetic acid (12% v/v) was added 1.25 g of 5% rhodium on alumina (50% w/w), the mixed slurry was saturated with hydrogen at 55 PSI and shaken for a total of 72 hrs. Upon completion of the hydrogenation the reaction was filtered through Celite and dried over anhydrous sodium sulfate. Filtration and subsequent rotoevaporation yielded crude product, which was then subjected to silica gel chromatographic purification to provide dimethyl aminocyclohexyldicarboxylate as a pale white solid. See also: Fieser & Fieser, Reagents for Org. Syn. 4, 418 and Freifelder, M.; Ng, Y. H.; Helgren, P. F.; *J. Org. Chem.*, 30, 2485–6.

Step K: Formation of Azide

The Halide (5.5 mmole) was dissolved in dry DMF and sodium azide (6.88 mmole) was added. The reaction was stirred overnight under nitrogen at 40° C. Workup: the reaction was concentrated under vacuum and partitioned between ethyl acetate and water. The organic layer was dried by MgSO$_4$. The azide product was obtained in 89% yield.

Step L: Reduction of Azide

The azide (2.44 mmole) was dissolved in THF, and PtO$_2$ (catalytic amount). The reaction was shaken on a Parr shaker in the presence of hydrogen (20–30 psi) for one hour. Workup: Filtered through celite and was rinsed with methanol. The filtrate was concentrated down to obtain the desired amine product in 92% yield.

Step M: Proctection of Amine

The amine (9.9 mmole) and triethylamine (9.9 mole) was dissolved in dry dichloromethane and (Boc)$_2$O was added. The reaction was stirred overnight under nitrogen. Workup: the reaction was concentrated on a rotary evaporator and the residue was taken up with ethyl acetate and then washed with water, citric acid, sodium bicarbonate, and brine. The organic solvent was dried over MgSO$_4$ (86%).

Step N: N-Methylation

The amine (4.1 mmole) was dissolved in THF and methyl iodide was added, followed by sodium hydride. The reaction was stirred overnight under nitrogen. Workup: the reaction was concentrated on a rotary evaporator and the residue was taken up with ethyl acetate and then washed with water, citric acid, sodium bicarbonate, and brine. The organic solvent was dried over MgSO$_4$.

Step 0: Bromination

The methyl ester (26.9 mmole), benzoyl peroxide (0.455 mmole), and NBS (26.9 mmole) were dissolved in benzene and kept at reflux overnight under N$_2$, after which the solution was concentrated to dryness. The remaining solid was filtered and washed with hot water, then dried on high vacuum overnight (81%).

Steps K, L and O are employed in the order set forth below:

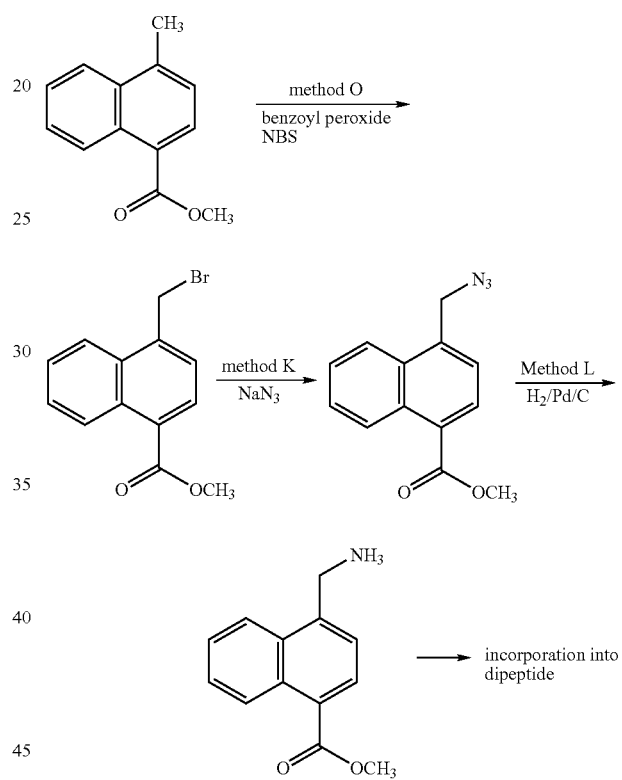

Mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

For the purpose of classification of the inhibitor activities of the compounds of the present invention, the Examples given below have been grouped by their IC$_{50}$ concentrations. Those compounds of Group IV have an IC$_{50}$ of greater than 200 μM. The compounds of Group III have an IC$_{50}$ concentration of from between 100 μM and 200 μM and are the preferred compounds of the invention. The compounds of Group II have an IC$_{50}$ concentration of from between 10 μM and 99 μM and are the more preferred compounds of the invention. The compounds of Group I have an IC$_{50}$ concentration of <10 μM and are the most preferred compounds of the invention.

TABLE 1
Enzyme inhibition assay results for structures having the peptide backbone:
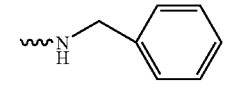
In Examples 1–26: $R_2$ is 2-methylpropyl, $R_3$ is methylthioethyl and A is tert-butyloxycarbonyl.
| Example | IC$_{50}$ Group | B |
|---|---|---|
| 1 | IV | —OMe |
| 2 | III | —OH |
| 3 | IV | 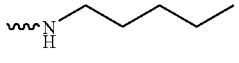 |
| 4 | IV | 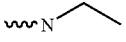 |
| 5 | III | 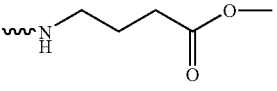 |
| 6 | II | 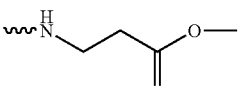 |
| 7 | III | 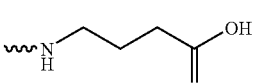 |
| 8 | II | 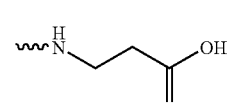 |
| 9 | II | 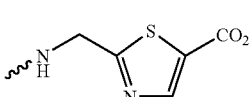 |
| 10 | II | 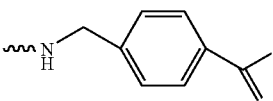 |
| 11 | I | 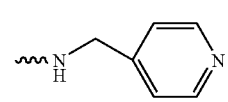 |
| 12 | III | 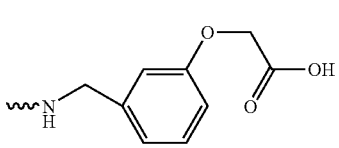 |
| 13 | I | 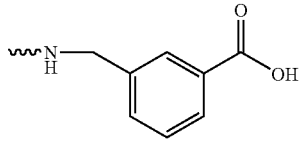 |
| 14 | I | 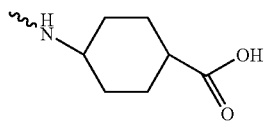 |
| 15 | I | 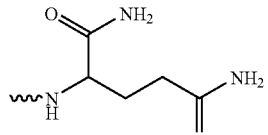 |
| 16 | IV | 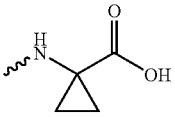 |
| 17 | II | 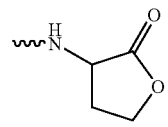 |
| 18 | II | 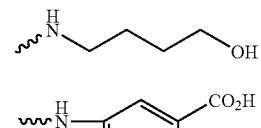 |
| 19 | III | 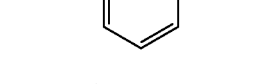 |
| 20 | II | 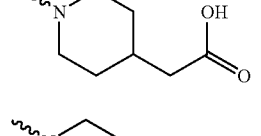 |
| 21 | II | 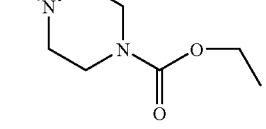 |
| 22 | III | 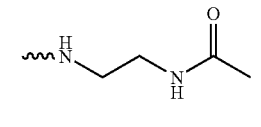 |
| 23 | III | 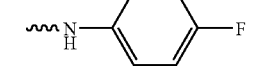 |
| 24 | III | 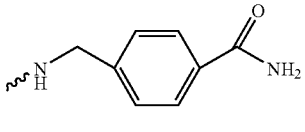 |
| 25 | II |  |

TABLE 1-continued

| | | |
|---|---|---|
| 26 | I | [structure: cyclohexane with N-H and two CO₂H groups] |
| 27 | II | [structure: cyclohexane with N-H and two CO₂H groups] |
| 28 | I | [structure: cyclohexane with N-H and CH₂CO₂H] |
| 29 | II | [structure: N-CH₂-phenyl-CO₂H with methyl on N] |
| 30 | I | [structure: N-H-CH with two CO₂H groups] |
| 31 | II | [structure: N-H-CH(CH₃)-phenyl-CO₂H] |
| 32 | I | [structure: cyclohexane with N-H and two CO₂H groups] |
| 33 | no data | [structure: hydroxyindane with N-H] |
| 34 | I | [structure: cyclohexane with N-H and CO₂H] |
| 35 | II | [structure: N-H-CH(phenyl)-CO₂H] |
| 36 | I | [structure: N-H-CH₂CH₂-phenyl with OH and NO₂] |

Table 1 continued for variations of amino acid substituents and/or N-terminal capping groups.

| R | IC₅₀ Group | Structure |
|---|---|---|
| 37 | I | $R_2$ is benzyl, $R_3$ is phenyl, A is acetyl and B is 4-aminomethyl-benzoic acid |
| 38 | II | $R_2$ is 2-methylpropyl, $R_3$ is phenyl, A is benzyloxycarbonyl and B is 4-aminomethyl-benzoic acid |
| 39 | II | $R_2$ is 2-methylpropyl, $R_3$ is phenyl, A is butyloxycarbonyl and B is 4-aminomethylbenzoic acid |

The following non-limiting examples describe a method by which each of the compounds of Table 1 and as numbered therein were prepared following the procedure outlined generally in Scheme 1.

EXAMPLE 1

Steps A through F were employed, substituting H₂N-Val-OMe (the methyl ester) for the benzyloxycarbonyl protected starting material, and selecting L-Met as AA₁ and L-Val as AA₂.

| | |
|---|---|
| Molecular Formula | $C_{29}H_{54}N_4O_8S$ |
| Molecular Weight | 618.87 |
| H-nmr (solvent) | (CDCl₃) δ 7.43(d, 1H); 7.20(d, 1H); 5.99(d, 1H); 5.20(d, 1H); 4.50(m, 1H); 3.90–3.80(m, 1H); 3.66(s, 3H); 2.50–2.30(m, 6H); 2.1–1.90(m, 6H); 1.56(m, 2H); 1.44(s, 9H); 0.99(m, 18H) |
| C-nmr (solvent) | (CDCl₃) δ 190.067, 172.229, 168.561, 117.913, 70.817, 70.574, 60.181, 57.383, 52.124, 40.916, 40.234, 30.123, 128.187, 24.778, 23.022, 21.706, 19.119, 18.978, 17.802, 15.169 |
| Mass spec (MH+) | 619.2 |

EXAMPLE 2

The product of Example 1 was further subjected to Step G to remove the methyl ester, leaving the free C-terminal acid.

| | |
|---|---|
| Molecular Formula | $C_{28}H_{52}N_4O_8S$ |
| Molecular Weight | 604.80 |
| H-nmr (solvent) | (CD₃OD) δ 8.33(d, 1H); 7.00(d, 1H); 4.55(m, 1H); 4.33(d, 2H); 4.1–3.8(m, 4H); 2.50(m, 2H); 2.42(d, 2H); 2.10(m, 2H); 2.08(s, 2H); 2.00(s, 3H); 1.55(m, 3H); 1.44(s, 9H); 1.33(m, 1H); 0.99(m, 18H) |
| C-nmr (solvent) | (CD₃OD) δ 194.624, 174.332, 173.972, 100.478, 71.737, 71.612, 59.118, 54.142, 52.699, 41.727, 41.256, 31.741, 31.498, 31.130, 28.716, 26.012, 25.824, 23.755, 22.563, 22.164, 20.667, 19.781, 19.540, 18.574, 18.261 |
| Mass spec (MH+) | 605 |

EXAMPLE 3

Steps A through F were employed, selecting L-Met as AA₁ and L-Val as AA₂ and using benzylamine as RNH₂ in step F.

| | |
|---|---|
| Molecular Formula | $C_{35}H_{59}N_5O_7S$ |
| Molecular Weight | 693.91 |

| | -continued |
|---|---|
| H-nmr (solvent) | (DMSO-d) δ 7.88(d, 1H); 7.77(d, 1H); 7.41(d, 1H); 7.34(m, 5H); 6.88(d, 1H); 4.88(d, 1H); 4.45(m, 1H); 4.36(d, 2H); 3.88(m, 2H); 3.45(s, 2H); 2.44(m, 2H); 2.22(m, 2H); 2.10(s, 3H); 1.9–1.80(m, 2H); 1.50(m, 3H); 1.44(s, 9H); 1.38(m, 1H); 0.98(m, 18H) |
| C-nmr (solvent) | (DMSO-d) δ 172.190, 171.846, 171.665, 140.236, 128.864, 127.915, 127.359, 78.734, 58.474, 51.224, 42.642, 32.617, 30.760, 30.070, 28.714, 24.748, 23.816, 22.287, 19.763, 18.674, 18.447, 15.197 |
| Mass spec (MH+) | 694 |

EXAMPLE 4

Steps A through F were employed, selecting L-Met as $AA_1$ and L-Val as $AA_2$ and using 1-pentanamine as $RNH_2$ in step F.

| | |
|---|---|
| Molecular Formula | $C_{33}H_{63}N_5O_7S$ |
| Molecular Weight | 673.95 |
| H-nmr (solvent) | (DMSO-d) δ 7.89(d, 1H); 7.66(d, 1H); 7.44(d, 1H); 6.88(d, 1H); 4.88(d, 1H); 4.45(m, 1H); 3.78(m, 2H); 3.1–3.0(m, 2H); 2.50(m, 2H); 2.22(d, 1H); 2.04(s, 3H); 2.0–1.80(m, 2H); 1.55(m, 3H); 1.44(s, 9H); 1.32(t, 3H); 0.98(m, 18H) |
| C-nmr (solvent) | (DMSO-d) δ 187.944, 183.453, 171.657, 164.00, 156.194, 117.413, 114.615, 117.413, 114.615, 100.429, 61.405, 58.435, 51.169, 32.656, 30.830, 30.054, 29.216, 29.106, 28.714, 24.748, 23.831, 22.303, 19.209, 18.494, 15.178, 14.371 |
| Mass spec (MH+) | 674 |

EXAMPLE 5

Steps A through F were employed, selecting L-Met as $AA_1$ and L-Val as $AA_2$ and using ethylamine as $RNH_2$ in step F.

| | |
|---|---|
| Molecular Formula | $C_{30}H_{57}N_6O_7S$ |
| Molecular Weight | 631.87 |
| H-nmr (solvent) | (CDCl₃) δ 7.66(bs, 1); 7.44(bs, 1H); 7.20(s, 1H); 7.10(bs, 1H); 5.20(bs, 1H); 4.55(bs, 1H); 4.1–3.9(m, 5H); 3.66(s, 1H); 3.4–3.20(m, 2H); 2.6–2.40(m, 5H); 2.20–1.99(m, 5H); 1.66(bs, 1H); 1.44(s, 9H); 1.40(s, 1H); 1.20(m, 3H); 0.99(m, 18H) |
| C-nmr (solvent) | (CDCl₃) δ 200.280; 190.067; 172.589; 172.001; 152.799; 149.272; 59.758; 58.242; 34.246; 30.233; 29.567; 28.219; 24.739; 22.967; 21.909; 19.292; 19.022; 17.826; 15.185; 14.628 |
| Mass spec (MH+) | 632.2 |

EXAMPLE 6

Steps A through F were employed, selecting L-Met as $AA_1$ and L-Val as $AA_2$ and using methyl 4-aminobutanoate as $RNH_2$ in step F.

| | |
|---|---|
| Molecular Formula | $C_{33}H_{61}N_5O_9S$ |
| Molecular Weight | 703.93 |
| H-nmr (solvent) | (DMSO-d) δ 4.88(d, 1H); 4.44(m, 1H); 4.11(m, 2H); 3.88(m, 3H); 3.66(s, 3H); 3.44(d, 2H); 3.10(m, 2H); 2.43(m, 1H); 2.25(t, 2H); 2.14(d, 2H); 2.04(s, 3H); 1.88(m, 2H); 1.60(t, 2H); 1.44(s, 9H); 1.40(m, 1H); 0.98(m, 18H) |
| C-nmr (solvent) | (DMSO-d) δ 173.821, 172.089, 171.657, 78.750, 60.417, 58.456, 52.367, 51.757, 51.091, 32.617, 31.277, 30.728, 30.619, 30.078, 28.714, 24.983, 24.756, 23.784, 22.303, 19.724, 19.693, 18.674, 18.494, 15.478 |
| Mass spec (MH+) | 704 |

EXAMPLE 7

Steps A through F were employed, selecting L-Met as $AA_1$ and L-Val as $AA_2$ and using methyl 3-aminopropanoate as $RNH_2$ in step F.

| | |
|---|---|
| Molecular Formula | $C_{32}H_{59}N_5O_9S$ |
| Molecular Weight | 689.91 |
| H-nmr (solvent) | (DMSO-d) δ 8.11(d, 1H); 7.98(d, 1H); 7.66(d, 1H); 7.55(d, 1H); 6.88(d, 1H); 4.88(d, 1H); 4.43(m, 1H); 4.14(m, 1H); 3.77(m, 3H); 3.66(s, 3H); 2.55(m, 4H); 2.54(m, 2H); 2.21(d, 2H); 2.01(s, 3H); 1.89(m, 2H); 1.45(m, 1H); 1.44(s, 9H); 1.33(m, 1H); 0.98(m, 18H) |
| C-nmr (solvent) | (DMSO-d) δ 205.602, 177.567, 172.747, 171.634, 114.615, 100.421, 78.750, 59.790, 58.348, 51.867, 51.108, 35.282, 34.099, 30.799, 30.070, 28.714, 23.855, 22.721, 19.732, 19.622, 18.721, 18.462, 18.313, 15.186 |
| Mass spec (MH+) | 689.9 |

EXAMPLE 8

The product of Example 6 was further subjected to Step G to remove the methyl ester, leaving the free C-terminal acid.

| | |
|---|---|
| Molecular Formula | $C_{32}H_{69}N_5O_9S$ |
| Molecular Weight | 689.91 |
| H-nmr (solvent) | (CD₃OD) δ 4.56(m, 1H), 4.20(m, 1H); 4.01–3.98(m, 2H); 3.32(m, 2H); 2.50(m, 2H); 2.24(m, 2H); 2.10(m, 3H); 2.00(m, 4H); 1.88(t, 2H); 1.55(m, 1H); 1.44(s, 9H); 1.44(s, 9H); 1.34(m, 1H); 0.99(m, 18H) |
| C-nmr (solvent) | (CD₃OD) δ 173.682, 74.206, 71.408, 54.463, 43.827, 41.444, 39.752, 32.188, 31.397, 31.185, 28.716, 25.730, 23.598, 22.305, 20.635, 19.656, 18.605, 18.206, 15.235 |
| Mass spec (MH+) | 690.1 |

EXAMPLE 9

The product of Example 7 was further subjected to Step G to remove the methyl ester leaving the free C-terminal acid.

| | |
|---|---|
| Molecular Formula | $C_{31}H_{57}N_5O_9S$ |
| Molecular Weight | 675.89 |
| H-nmr (solvent) | (CD₃OD) δ 4.45(m, 1H); 4.1–4.0(m, 2H); 4.0–3.98(m, 3H); 3.54(m, 2H); 2.56(m, 3H); 2.40(m, 2H); 2.1–2.0(m, 4H); 1.66(m, 2H); 1.44(m, 11H); 1.22(t, 2H); 0.98(m, 18H) |

-continued

| | |
|---|---|
| C-nmr (solvent) | (CD$_3$OD) δ 174.231, 173.666, 100.478, 74.167, 71.392, 43.804, 41.562, 36.413, 34.547, 32.627, 31.444, 31.185, 30.856, 28.724, 25.855, 23.622, 22.266, 19.758, 15.259 |
| Mass spec (MH+) | 676 |

EXAMPLE 10

Steps A through F were employed, selecting L-Met as AA$_1$ and L-Val as AA$_2$ and using methyl 2-aminomethylthiazole-5-carboxylate as RNH$_2$ in step F and then removal of the methyl ester according to step G. The methyl 2-aminomethylthizaole-5-carboxylate was prepared according to Synthesis 1986, page 992.

| | |
|---|---|
| Molecular Formula | C$_{33}$H$_{56}$N$_6$O$_9$S |
| Molecular Weight | 744.98 |
| H-nmr (solvent) | (CD$_3$OD) δ 9.10(m, 1H); 8.88(m, 1H); 8.26(s, 1H); 7.55(m, 1H); 4.78(m, 2H); 4.65(m, 1H); 4.33(m, 2H); 4.1–3.9(m, 3H); 3.33(2H); 2.50–2.10(m, 4H); 2.10–1.90(m, 4H); 1.60(m, 1H); 1.44(m, 10H); 1.30(m, 1H); 0.99(m, 18H) |
| C-nmr (solvent) | (CD$_3$OD) δ 168.351, 123.778, 65.278, 54.203, 26.316, 25.603, 25.164, 24.827, 22.810, 22.672, 21.810, 19.780, 17.664, 16.229, 16.127, 13.593, 12.499, 12.224, 11.981, 9.99 |
| Mass spec (MH+) | 745.2 |

EXAMPLE 11

Steps A through F were employed, selecting L-Met as AA$_1$ and L-Val as AA$_2$ and using methyl 4-aminomethylbenzoate as RNH$_2$ in step F and then removal of the methyl ester according to step G.

| | |
|---|---|
| Molecular Formula | C$_{36}$H$_{59}$N$_5$O$_9$S |
| Molecular Weight | 737.96 |
| H-nmr (solvent) | (MeOD) δ 8.88(m, 1H); 7.88(d, 2H); 7.44(d, 2H); 4.55(m, 2H); 4.22(m, 1H); 4.0–3.9(m, 2H); 2.5–2.3(m, 3H); 2.14(m, 1H); 2.0–1.9(m, 4H); 1.55(m, 1H); 1.44(s, 9H); 1.33(m, 1H); 0.99(m, 18H) |
| C-nmr (solvent) | (MeOD) δ 171.99, 171.157, 171.027, 166.761, 142.554, 127.964, 127.759, 125.447, 77.899, 68.452, 59.114, 57.750, 51.573, 49.165, 40.875, 38.712, 38.401, 29.334, 28.611, 28.415, 28.266, 25.803, 22.953, 20.715, 19.348, 16.862, 16.797, 15.747, 15.235, 12.314 |
| Mass spec (MH+) | 738.3 |

EXAMPLE 12

Steps A through F were employed, selecting L-Met as AA$_1$ and L-Val as AA$_2$ and using methyl 4-aminomethylpyridine as RNH$_2$ in step F.

| | |
|---|---|
| Molecular Formula | C$_{34}$H$_{58}$N$_6$O$_7$S |
| Molecular Weight | 694.94 |
| Mass spec (MH+) | 695.2 |

EXAMPLE 13

Steps A through F were employed, selecting L-Met as AA$_1$ and L-Val as AA$_2$ and using methyl 4-aminomethylbenzoxyacetate as RNH$_2$ in step F and then removal of the methyl ester according to step G. Methyl 4-aminomethylbenzoxyacetate was prepared according to the procedure provided in J. Med. Chem. 1998, Vol. 31, No. 10

| | |
|---|---|
| Molecular Formula | C$_{37}$H$_{61}$N$_5$O$_{10}$S |
| Molecular Weight | 767.99 |
| H-nmr (solvent) | (MeOD): δ 7.25 (t, 1H), 6.98 (m, 2H), 6.77 (s, 2H), 4.77 (s, 2H), 4.44 (m, 1h), 4.32 (m, 1h), 3.8 (m, 3H), 3.33 (s, 2h), 2.4 (m, 5 H), 2.1 (m, 1H), 1.66 (m, 1h), 1.44 (s, 9h), 0.99 (m, 18H) |
| C-nmr (solvent) | (MeOD): δ 169.033, 168.178, 167.998, 167.873, 166.744, 153.686, 135.801, 124.671, 124.617, 120.227, 115.650, 108.690, 108.463, 74.839, 65.411, 59.815, 55.935, 53.802, 54.548, 54.344, 48.403, 48.074, 46.067, 35.651, 35.463, 35.322, 26.489, 26.144, 25.642, 25.501, 25.345, 25.078, 24.819, 22.711, 19.741, 17.664, 16.206, 13.729, 13.588, 12.593, 12.216, 9.246 |
| Mass spec (MH+) | 768 |

EXAMPLE 14

Steps A through F were employed, selecting L-Met as AA$_1$ and L-Val as AA$_2$ and using methyl 3-aminomethylbenzoate as RNH$_2$ in step F and then removal of the methyl ester according to step G.

| | |
|---|---|
| Molecular Formula | C$_{36}$H$_{59}$N$_5$O$_9$S |
| Molecular Weight | 737.96 |
| H-nmr (solvent) | (CD$_3$OD/CDCl$_3$) δ 8.0(s, 1H); 7.89(d, 1H); 7.89(s, 1H); 7.66(s, 1H); 7.55(d, 1H); 7.50(d, 1H); 7.44(t, 1H); 6.88(d, 1H); 6.77(d, 1H); 4.6–4.4(m, 3H); 4.33(m, 1H); 4.0–3.8(m, 3H); 2.5–2.3(m, 4H); 2.22(m, 1H); 2.1–1.9(m, 5H); 1.5–1.4((m, 11H); 1.40(m, 1H); 0.99(m, 18H) |
| C-nmr (solvent) | (CD$_3$OD/CDCl$_3$) δ 169.088, 168.123, 168.045, 139.924, 134.445, 126.984, 124.217, 123.684, 75.255, 56.053, 54.603, 48.685, 45.942, 35.698, 35.494, 29.444, 25.932, 25.650, 25.292, 25.227, 25.078, 24.106, 23.032, 19.866, 17.899, 16.527, 14.019, 12.859, 12.449, 12.271, 9.583 |
| Mass spec (MH+) | |

EXAMPLE 15

Steps A through F were employed, selecting L-Met as AA$_1$ and L-Val as AA$_2$ and using methyl 4-aminocyclohexylcarboxylate as RNH$_2$ in step F and then removal of the methyl ester according to step G.

| | |
|---|---|
| Molecular Formula | C$_{35}$H$_{63}$N$_5$O$_9$S |
| Molecular Weight | 729.97 |
| H-nmr (solvent) | (CD$_3$OD) δ 8.34(d, 1H); 8.11(d, 1H); 7.98(d, 1H); 7.55(d, 1H); 6.88(d, 1H); 4.55(m, 1H); 4.23(m, 1H); 3.9–3.8(m, 5H); 3.34(m, 1H); 2.6–2.5(m, 3H); 2.32(D, 2H); 2.0(S, 3H); 1.98(M, 2H); 1.67(m, 8H); 1.44(s, 9H); 1.33(m, 1H); 0.99(m, 18H) |
| C-nmr (solvent) | (CD$_3$OD) δ 172.991, 168.241, 168.163, 167.849, 167.222, 74.761, 65.419, 54.383, 48.191, 46.663, 35.463, 35.236, 34.726, 26.387, 25.870, 25.055, 24.091, 22.688, 20.258, 19.795, 17.671, 16.237, 13.753, 12.616, 12.428, 9.183 |
| Mass spec (MH+) | 730.5 |

EXAMPLE 16

Steps A through F were employed, selecting L-Met as $AA_1$ and L-Val as $AA_2$ and using 2-aminoglutaramide as $RNH_2$ in step F.

| | |
|---|---|
| Molecular Formula | $C_{33}H_{61}N_7O_9S$ |
| Molecular Weight | 731.96 |
| H-nmr (solvent) | $(CD_3OD)$ δ 8.44(d, 1H); 8.22(d, 1H); 7.86(d, 1H); 6.88(m, 1H); 4.56(m, 1H); 4.33(m, 1H); 4.0–3.9(m, 3H); 3.33(m, 2H); 2.55(m, 2H); 2.43(m, 2H); 2.1–1.9(m, 5H); 1.55(m, 1H); 1.44(s, 9H); 1.33(m, 1H); 0.99(m, 18H) |
| C-nmr (solvent) | $(CD_3OD)$ δ 174.129, 96.505, 80.711, 71.549, 61.971, 59.440, 59.283, 54.189, 52.786, 52.480, 41.437, 32.525, 31.640, 28.700, 25.785, 23.786, 22.211, 22.140, 19.781, 19.475, 18.621, 18.449, 15.235 |
| Mass spec (MH+) | 731 |

EXAMPLE 17

Steps A through F were employed, selecting L-Met as $AA_1$ and L-Val as $AA_2$ and using methyl 1-aminocyclopropane-1-carboxylate as $RNH_2$ in step F and then removal of the methyl ester according to step G.

| | |
|---|---|
| Molecular Formula | $C_{32}H_{57}N_5O_9S$ |
| Molecular Weight | 687.90 |
| Mass spec (MH+) | 688 |

EXAMPLE 18

Steps A through F were employed, selecting L-Met as $AA_1$ and L-Val as $AA_2$ and using 3-amino-dihydro-2(3H)-furanone as $RNH_2$ in step F.

| | |
|---|---|
| Molecular Formula | $C_{32}H_{57}N_5O_9S$ |
| Molecular Weight | 687.90 |
| Mass spec (MH+) | 688.4 |

EXAMPLE 19

Steps A through F were employed, selecting L-Met as $AA_1$ and L-Val as $AA_2$ and using methyl 4-aminobutan-1-ol as $RNH_2$ in step F.

| | |
|---|---|
| Molecular Formula | $C_{32}H_{61}N_5O_8S$ |
| Molecular Weight | 675.92 |
| H-nmr (solvent) | $(CD_3OD)$ δ 8.33(m, 1H); 8.11(m, 1H); 4.55(m, 1H); 4.11(m, 1H); 4.0–3.9(m, 2H); 3.55(m, 2H); 3.33(m, 2H); 3.30(m, 2H); 2.55(m, 2H); 2.1–1.9(m, 4H); 1.66(m, 2H); 1.44(s, 9H); 1.33(m, 1H); 0.99(m, 18H) |
| Mass spec (MH+) | 676 |

EXAMPLE 20

Steps A through F were employed, selecting L-Met as $AA_1$ and L-Val as $AA_2$ and using methyl 3-aminobenzoate as $RNH_2$ in step F and then removal of the methyl ester according to step G.

| | |
|---|---|
| Molecular Formula | $C_{35}H_{57}N_5O_9S$ |
| Molecular Weight | 723.94 |
| Mass spec (MH+) | 724 |

EXAMPLE 21

Steps A through F were employed, selecting L-Met as $AA_1$ and L-Val as $AA_2$ and using methyl 4-piperidine-acetate as $RNH_2$ in step F and then removal of the methyl ester according to step G.

| | |
|---|---|
| Molecular Formula | $C_{35}H_{63}N_5O_9S$ |
| Molecular Weight | 729.98 |
| H-nmr (solvent) | $(CD_3OD)$ δ 8.22(m, 1H); 7.66(m, 1H); 6.88(d, 1H); 4.87(m, 1H); 4.55(m, 1H); 4.0–3.8(m, 3H); 3.22(m, 2H); 2.6–2.3(m, 2H); 2.22(m, 2H); 2.15(m, 1H); 2.0–1.9(m, 5H); 1.77(m, 1H); 1.55(m, 1H); 1.44(m, 9H); 1.33(m, 1H); 0.99(18H) |
| C-nmr (solvent) | $(CD_3OD)$ δ 173.964, 166.095, 126.225, 80.680, 71.447, 61.854, 61.854, 55.427, 54.165, 43.404, 42.283, 41.444, 41.045, 34.320, 33.646, 32.510, 31.890, 31.067, 30.824, 28.685, 25.785, 23.739, 22.179, 20.040, 19.765, 18.574, 18.425, 18.221, 15.227 |
| Mass spec (MH+) | 730 |

EXAMPLE 22

Steps A through F were employed, selecting L-Met as $AA_1$ and L-Val as $AA_2$ and using ethyl piperazine-$N^1$-carboxylate as $RNH_2$ in step F and then removal of the ethyl ester according to step G.

| | |
|---|---|
| Molecular Formula | $C_{35}H_{64}N_6O_9S$ |
| Molecular Weight | 744.98 |
| H-nmr (solvent) | $(CD_3OD)$ δ 7.55(d, 1H); 4.66(d, 2H); 4.55(m, 1H); 4.12(m, 2H); 4.1–3.8(m, 4H); 3.5–3.2(m, 4H); 2.55(m, 2H); 2.20(m, 2H); 2.1–1.90(m, 5H); 1.66(m, 1H); 1.411(s, 9H); 1.33(m, 4H); 0.99(m, 18H) |
| C-nmr (solvent) | $(CD_3OD)$ δ 174.873, 174.011, 173.925, 173.847, 172.592, 157.231, 80.688, 71.455, 62.967, 61.791, 55.631, 54.126, 52.942, 49.878, 49.306, 49.024, 46.837, 43.020, 41.382, 41.154, 32.619, 31.726, 31.107, 28.755, 23.802, 22.250, 19.820, 18.668, 18.558, 15.290, 14.883 |
| Mass spec (MH+) | 745.4 |

EXAMPLE 23

Steps A through F were employed, selecting L-Met as $AA_1$ and L-Val as $AA_2$ and using 1-acetamido-2-aminoethane as $RNH_2$ in step F.

| | |
|---|---|
| Molecular Formula | $C_{32}H_{60}N_6O_8S$ |
| Molecular Weight | 688.93 |
| H-nmr (solvent) | (MeOD): δ 8.33 (m, 2H); 8.01 (d, 1H), 7.66 (d, 1h), 6.88 (d, 1h), 4.56 (m, 1H), 4.22 (m, 1H), 3.8 (m, 3h), 3.44 (m, 2H), 2.56 (m, 2H), 2.33 (d, 2H), 2.2 (m, 8H), 1.66 (m, 1H), 1.44 (s, 9H), 1.33 (m, 1H), 0.99 (m, 18H) |
| C-nmr (solvent) | (MeOD): δ 194.616, 174.466, 155.044, 96.512, 76.275, 60.764, 54.400, 52.182, 41.562, 41.280, 39.916, 32.345, 31.579, 31.248, 31.154, 28.693, 25.816, 23.637, 22.650, 22.281, 19.750, 19.632, 18.613, 18.143, 15.204 |
| Mass spec (MH+) | 689 |

EXAMPLE 24

Steps A through F were employed, selecting L-Met as $AA_1$ and L-Val as $AA_2$ and using 1-amino 4-fluorobenzene as $RNH_2$ in step F.

| | |
|---|---|
| Molecular Formula | $C_{34}H_{56}N_5O_7S$ |
| Molecular Weight | 697.91 |
| H-nmr (solvent) | (MeOD): δ 7.66 (m, 1H), 7.00 (m, 1H), 4.55 (m, 1H), 4.34 (m, 1H), 4.22 (d, 2H), 4.0 (m, 4H), 3.22 (s, 9H), 2.66 (m, 2H), 2.45 (m, 2H), 1.9 (m, 5H), 1.66 (m, 1H), 1.44 (s, 9H), 1.33 (m, 1H), 0.99 (18H) |
| Mass spec (MH+) | 699 |

EXAMPLE 25

Steps A through F were employed, selecting L-Met as $AA_1$ and L-Val as $AA_2$ and using 4-aminomethylbenzocarboxamide as $RNH_2$ in step F.

| | |
|---|---|
| Molecular Formula | $C_{36}H_{60}N_6O_8S$ |
| Molecular Weight | 736.98 |
| H-nmr (solvent) | (CD$_3$OD) δ 8.22(d, 1H); 7.67(d, 2H); 7.44(d, 2H); 4.55(m, 1H); 4.0–3.90(m, 2H); 3.22(m, 2H); 3.10(m, 4H); 2.5–2.4(m, 3H); 2.01(d, 3H); 1.66(m, 1H); 1.44(s, 9H); 0.99(m, 18H) |
| C-nmr (solvent) | (CD$_3$OD) δ 169.147; 168.539; 168.48; 168.312; 168.139; 168.053; 166.211; 152.479; 138.481; 138.317; 127.665; 123.010; 122.971; 122.602; 122.555; 74.855; 65.419; 56.084; 54.673; 54.446; 48.238; 48.238; 46.640; 45.958; 37.548; 35.541; 35.541; 35.267; 35.157; 26.644; 25.486; 25.282; 25.109; 22.672; 19.788; 17.601; 16.073; 13.659; 12.616; 12.240; 9.144; 3.054 |
| Mass spec (MH+) | 737.4 |

EXAMPLE 26

Steps A through F were employed, selecting L-Met as $AA_1$ and L-Val as $AA_2$ and using 3,5-dicarboxycyclohexylamine as $RNH_2$ in step F. The amine was prepared as follows: To 2.5 g of dimethyl 5-aminoisophthalate in 40 ml of methanol/4.8 ml acetic acid (12% v/v) was added 1.25 g of 5% rhodium on alumina (50% w/w), the mixed slurry was saturated with hydrogen at 55 PSI and shaken for a total of 72 hrs. Upon completion of they hydrogenation the reaction was filtered through Celite and dried over anhydrous sodium sulfate. Filtration and subsequent rotoevaporation yielded 3.85 g of crude product, which was then subjected to silica gel chromatographic purification to afford 0.76 g of Di-Methyl 1-Aminocyclohexyl-3,5-Di-Carboxylate as a pale white solid. See also: Fieser & Fieser, Reagents for Org. Syn. 4, 418 and Freifelder, M.; Ng, Y. H.; Helgren, P. F.; *J. Org. Chem.,* 30, 2485–6.

| | |
|---|---|
| Molecular Formula | $C_{36}H_{63}N_5O_{11}S$ |
| Molecular Weight | 773 |
| tlc Rf (solvent) | Rf = 0.05 (10% MeOH/DCM) |
| Purification: | 1. Acid/Base Washes. 2. Trituration w/Ether/Filtration |
| Mass spec (MH+) | 772.3 (ESI Neg.) |
| Synthetic Route | Method A, B, E, J, F, G |
| Description | Method J: Amino-Aryl Diesters to Amino-Cyclohexyl Diesters |

EXAMPLE 27

Prepared in a manner similar to Example 26, except that dimethyl 6-aminoterephthalate was utilized in the preparation of 2,5-dicarboxycyclohexylamine.

| | |
|---|---|
| Molecular Formula | $C_{36}H_{63}N_5O_{11}S$ |
| Molecular Weight | 773 |
| tlc Rf (solvent) | Rf = 0.25 (10% MeOH/DCM) |
| Purification: | 1. Acid/Base Washes. 2. Trituration w/Ether/Filtration |
| Mass spec (MH+) | 774.4 (ESI -Positive) |
| Elemental Analysis -Calc (%) | |
| Found (%) | |
| Synthetic Route | Method A, B, E, J, F, G |
| Description | Method J: Amino-Aryl Diesters to Amino-Cyclohexyl Diesters |

EXAMPLE 28

Prepared using methyl 4-aminoocyclhexylacetate.

| | |
|---|---|
| Molecular Formula | $C_{36}H_{65}N_5O_9S$ |
| Molecular Weight | 744 |
| H-nmr (solvent) | (MeOD) δ 8.32(d, 1H); 8.00(d, 1H); 7.66(d, 1H); 4.66(m, 1H); 4.20(d, 2H); 4.0–3.88(m, 3H); 3.46(m, 2H); 2.66(m, 1H); 2.40(d, 2H); 2.30(d, 2H); 2.1–1.90(m, 4H); 1.77(m, 4H); 1.44(s, 9H); 1.33(m, 1H); 0.99(m, 18H) |
| C-nmr (solvent) | (MeOD) δ 177.003, 175.060, 174.197, 173.915, 173.194, 80.785, 71.427, 61.927, 60.422, 54.293, 52.631, 41.486, 41.204, 40.200, 33.256, 32.645, 32.598, 32.347, 31.845, 31.720, 31.594, 31.108, 29.509, 28.788, 28.710, 25.841, 23.678, 22.283, 19.775, 19.665, 18.615, 18.53, 15.197 |
| Mass spec (MH+) | 744 |
| Synthetic Route Description | Method F, J, G |

EXAMPLE 29

Prepared according to the initial preparation used to prepare Example 11 but Steps M and N are inserted prior to the removal of the ester alcohol. Aminomethylbenzoic acid was first protected with 1 equivalent of BOC and then the N-protected amine was methylated with methyl iodide. The BOC group was subsequently removed and the N-methylaminomethylbenzoic acid was coupled with the tetrapeptide.

| | |
|---|---|
| Molecular Formula | $C_{37}H_{61}N_5O_9S$ |
| Molecular Weight | 751.97 |
| H-nmr (solvent) | (MeOD) δ 8.10(m, 2H); 7.45(m, 2H); 4.66(m, 5H); 4.0–3.80(m, 4H); 3.20(m, 2H); 2.90(m, 3H); 2.60(m, 1H); 2.40(m, 2H); 2.2–2.0(m, 4H); 1.66(m, 1H); 1.44(s, 9H); 1.33(m, 1H); 0.99(m, 18H) |
| C-nmr (solvent) | (MeOD) δ 174.934, 174.448, 174.244, 174.041, 173.947, 169.714, 143.865, 131.418, 131.136, 128.816, 80.738, 71.583, 61.896, 61.770, 56.190, 55.939, 54.152, 53.039, 52.098, 49.857, 41.470, 36.078, 36.046, 32.519, 32.018, 31.093, 28.694, 25.810, 23.709, 22.173, 19.775, 19.634, 18.615, 18.427, 15.229 |
| Mass spec (MH+) | 752 |
| Synthetic Route Description | Method F, M, N, G |

EXAMPLE 30

The amine utilized was dimethyl 1-amino-1,3-propanedicarboxylate and then the dicarboxylate was saponified to provide the dicarboxylic acid.

| | |
|---|---|
| Molecular Formula | $C_{33}H_{59}N_5O_{11}S$ |
| Molecular Weight | 733.91 |
| H-nmr (solvent) | (MeOD) δ 8.45(d, 1H); 8.25(d, 1H); 7.60(d, 1H); 4.55(m, 1H); 4.25(d, 2H); 4.01–3.80(m, 3H); 3.40(m, 2H); 2.60(m, 1H); 2.60(m, 1H); 2.40(m, 2H); 2.2–1.9(m, 4H); 1.66(m, 1H); 1.44(s, 9H); 1.33(m, 1H); 0.99(m, 18H) |
| C-nmr (solvent) | (MeOD) δ 176.627, 175.012, 174.809, 174.244, 174.197, 173.978, 80.769, 71.505, 61.880, 60.218, 54.230, 52.913, 52.678, 41.517, 32.409, 31.688, 31.234, 31.077, 28.694, 27.644, 25.826, 23.741, 22.252, 19.759, 19.665, 18.615, 18.474, 15.213 |
| Mass spec (MH+) | 734 |
| Synthetic Route Description | Method F, G |

EXAMPLE 31

The tetrapeptide was coupled to the N-terminal capping group. The capping groups was prepared by reacting 1-bromo-1-(4-benzoic acid) ethane with sodium azide, reducing the resulting azide to the amine and coupling the product with the tetrapeptide.

| | |
|---|---|
| Molecular Formula | $C_{37}H_{61}N_5O_9S$ |
| Molecular Weight | 751.97 |
| H-nmr (solvent) | (MeOD/CCl$_3$D) δ 7.98(d, 2H); 7.36(m, 2H); 5.03(m, 1H); 4.66(m, 1H); 4.32(m, 2H); 4.0–3.9(m, 2H); 2.56(m, 1H); 2.1–1.9(m, 7H); 1.66(m, 1H); 1.44(s, 9H); 1.33(m, 1H); 0.99(m, 18H) |
| C-nmr (solvent) | (MeOD/CCl$_3$D) δ 174.244, 173.931, 132.562, 130.885, 130.039, 126.997, 71.536, 69.185, 41.517, 41.298, 40.106, 31.563, 30.089, 28.835, 25.888, 24.885, 24.007, 23.709, 22.424, 22.346, 19.822, 18.677, 15.339, 14.461, 11.435 |
| Mass spec (MH+) | 752 |
| Synthetic Route Description | Method F, K, L, G |

EXAMPLE 32

Prepared in a manner similar to Example 26, except that dimethyl 5-aminophthalate was utilized in the preparation of 3,4-dicarboxycyclohexylamine.

| | |
|---|---|
| Molecular Formula | $C_{36}H_{63}N_5O_{11}S$ |
| Molecular Weight | 773 |
| tlc Rf (solvent) | Rf = 0.19 (10% MeOH/DCM) |
| Purification: | 1. Acid/Base Washes. 2. Trituration w/Ether/Filtration |
| Mass spec (MH+) | 774.5 (ESI - Positive) |
| Synthetic Route Description | Method A, B, E, J, F, G Method J: Amino-Aryl Diesters to Amino-Cyclohexyl Diesters |

EXAMPLE 33

The tetrapeptide was coupled with 1-amino-indan-2-ol using step F.

| | |
|---|---|
| Molecular Formula | $C_{37}H_{61}N_5O_8S$ |
| Molecular Weight | 736 |
| H-nmr (solvent) | (MeOD) δ 7.99(m, 1H); 7.66(m, 1H); 7.4–7.2(b, 4H); 6.88(m, 1H); 5.33(b, 2H); 4.66(m, 1H); 4.50(m, 2H); 4.1–3.9(m, 3H); 3.33(b, 2H); 3.10(m, 1H); 3.0–2.9(m, 1H); 2.6–2.4(m, 2H); 2.22(m, 1H); 2.0–1.9(m, 4H); 1.44(s, 10H); 0.99(m, 18H) |
| C-nmr (solvent) | (MeOD) δ 168.484, 135.887, 123.057, 121.975, 120.274, 119.577, 68.060, 65.317, 55.747, 54.650, 52.753, 48.466, 46.906, 35.487, 35.150, 34.844, 26.340, 25.454, 25.031, 22.688, 19.788, 17.656, 16.229, 13.808, 12.577, 12.412, 9.207 |
| Mass spec (MH+) | 736 |
| Synthetic Route Description | Method F, |

EXAMPLE 34

The methyl ester of 2-carboxy-cyclohexylamine was prepared according to setp H, then coupled with the tetrapeptide and the free carboxlyic acid was generated according to step G.

| | |
|---|---|
| Molecular Formula | $C_{36}H_{63}N_6O_9S$ |
| Molecular Weight | 730 |
| H-nmr (solvent) | (MeOD) δ 8.35(m, 1H); 8.25(m, 1H); 7.65(m, 1H); 6.80(m, 1H); 4.65(m, 1H); 4.20(m, 2H); 4.0–3.90(m, 3H); 3.35(m, 2H); 2.6–2.40(m, 3H); 2.20(b, s, 2H); 1.77(m, 2H); 1.66(m, 2H); 1.44(s, (H); 1.33(m, 1H); 0.99(m, 18H) |
| C-nmr (solvent) | (MeOD) δ 172.991, 172.912, 168.163, 167.073, 74.785, 65.434, 54.509, 48.348, 46.381, 35.353, 29.953, 26.959, 26.849, 26.418, 25.109, 23.424, |

| | 23.354, 22.735, 19.286, 17.711, 16.433, 16.355, 13.808, 13.666, 12.663, 12.358, 9.238 |
|---|---|
| Synthetic Route Description | Method H, F, G |

EXAMPLE 35

The tetrapeptide was coupled with the methyl ester of phenylglycine and the ester group was subsequently removed.

| Molecular Formula | $C_{36}H_{59}N_5O_9S$ |
|---|---|
| Molecular Weight | 737 |
| H-nmr (solvent) | (MeOD) δ 7.44–7.30(m, 5H); 5.40(s, 1H); 4.55(m, 1H); 4.01(m, 2H); 3.98(m, 1H); 3.22(s, 2H); 2.44(m, 2H); 2.1–2.0(m, 5H); 1.66(m, 1H); 1.33(m, 1H); 0.99(m, 18H) |
| C-nmr (solvent) | (MeOD) δ 177.058, 123.794, 123.331, 122.924, 19.764, 17.679, 16.159, 13.729, 13.627, 12.553 |
| Mass spec (MH+) | 738 |
| Synthetic Route Description | Method F, G |

EXAMPLE 36

The tetrapeptide was coupled with 2-(5-(2-hydroxynitrobenzene))-1-ethanamine.

| Molecular Formula | $C_{36}H_{60}N_6O_{10}S$ |
|---|---|
| Molecular Weight | 768.98 |
| H-nmr (solvent) | (MeOD) δ 8.00(s, 1H); 7.66(d, 1H); 7.10(d, 1H); 4.55(m, 1H); 4.0–3.90(m, 3H); 3.55(M, 2H); 3.40(S, 2H); 2.80(m, 2H); 2.6–2.50(m, 2H); 2.40(m, 1H); 2.1–1.90(m, 4H); 1.60(m, 1H); 1.44(s, 9H); 1.30(m, 1H); 0.99(m, 18H) |
| C-nmr (solvent) | (MeOD) δ 169.174, 168.139, 168.037, 167.912, 152.479, 133.066, 129.562, 126.741, 120.079, 120.00, 115.133, 74.863, 65.897, 56.076, 54.634, 54.289, 48.513, 48.262, 46.663, 46.052, 35.283, 29.052, 29.005, 26.254, 25.486, 25.298, 25.486, 25.298, 25.172, 25.109, 22.680, 19.835, 17.711, 17.640, 16.253, 16.088, 13.596, 12.546, 12.075, 9.199 |
| Mass spec (MH+) | 769 |
| Synthetic Route Description | Method F |

EXAMPLE 37

The compound was prepared in a manner similar to Example 11 with the following variations: Phenyl-statine (Phe-Sta) was employed in place of statine and phenylglycine (Phg) was selected as $AA_1$ and N-Ac-L-Val was used as $AA_2$

| Molecular Formula | $C_{39}H_{49}N_5O_8$ |
|---|---|
| Molecular Weight | 715 |
| Mass spec (MH+) | 716.3 (APCI) |

EXAMPLE 38

The compound was prepared in a manner similar to Example 11 with the following variations: Phenylglycine (Phg) was selected as $AA_1$ and carbobenzyloxy (Cbz)-L-Val was selected as $AA_1$.

| Molecular Formula | $C_{42}H_{54}N_5O_9$ |
|---|---|
| Molecular Weight | 772.92 |
| H-nmr (solvent) | (DMSO): δ 8.635 (m, 1H), 8.461(m, 1H), 7.899 (d, 2H), 7.399 (m, 10H), 5.571 (m, 1H), 4.982 (m, 2H), 4.335 (m, 2H), 4.157 (m, 1H), 3.833 (m, 1H), 2.317 (d, 1H), 1.999 (m, 3H), 1.335 (m, 1H), 1.141 (m, 1H), 0.808 (m, 15H), 0.564 (d, 1H), 0.550 (d, 1H) |
| Mass spec (MH+) | 774 |

EXAMPLE 39

The compound was prepared in a manner similar to Example 11 with the following variation:

Phenylglycine (Phg) was selected as $AA_1$.

| Molecular Formula | $C_{39}H_{57}N_5O_9$ |
|---|---|
| Molecular Weight | 739.90 |
| H-nmr (solvent) | (MeOD): δ 8.88 (d, 1H), 8.66 (d, 1h), 8.44 (d, 1H), 7.99 (d, 2H), 7.66 (d, 1H), 7.5 (m, 6H), 5.55 (d, 1H), 4.55 (m, 1H), 4.34 (m, 2H), 3.8 (m, 3H), 3.55 (m, 1h), 3.44 (m, 2H), 2.55 (m, 2H), 2.2 (m, 2H), 1.55 (m, 1H), 1.44 (s, 9H), 1.33 (m, 1H), 0.99 (m, 18H) |
| C-nmr (solvent) | (MeOD): δ 168.210, 166.470, 139.696, 125.079, 124.734, 123.927, 123.721, 123.574, 123.433, 123.229, 122.884, 122.743, 122.594, 122.524, 74.628, 69.724, 55.574, 53.035, 46.036, 37.846, 37.744, 35.543, 35.369, 26.136, 25.517, 24.843, 23,793, 22.719, 22.625, 19.803, 19.631, 17.622, 17.546, 16.190, 15.955, 13.698, 13.729, 12.546, 12.342 |
| Mass spec (MH+) | 740 |

Enzyme Inhibition Assay

Purpose/Rationale:

The MBP-C125 assay, determines relative inhibition of β-secretase cleavage of an MPB-C125 substrate by the compounds assayed. Human brain β-Secretase from the concentrated HiQ pool prepared Jul. 16, 1997 in 0.20% Triton is used in the assay. Inhibition data was obtained from an ELISA which uses an anti-MBP capture antibody (on precoated and blocked 96-well high binding plates) followed by incubation with diluted enzyme reaction supernatant, incubation with an anti-SW192 specific biotinylated reporter antibody and incubation with streptavidin/alkaline phosphatase. Detection was effected by a fluorescent substrate signal on cleavage by the phosphatase. The ELISA only detected cleavage following Leu 596 at the substrate's Swedish APP 751 mutation site.

Compounds were diluted in a 1:1 dilution series to a six-point concentration curve (two wells per concentration) which took up one 96-plate row per compound tested. Relative compound inhibition potency was determined by calculating the concentration of compound that showed a fifty-percent reduction in detected signal compared to the enzyme reaction signal in the control wells with no added compound.

Procedure:

Each of the test compounds was weighed out into a vial and DMSO was added to make up a 10 mM solution. To obtain a final compound concentration of 200 μM at the high point of a 6-point dilution curve, 100 μL of the 10 mM solution was added to well C1 of a 96-well V-bottom plate. Fifty μL of DMSO was added to odd wells of row C across the plate and 1:1 serial dilutions were made. 10 μL of each dilution was added to each of two wells on row C of a corresponding V-bottom plate to which 190 μL of 52 mM NaOAc/7.9% DMSO, pH 4.5 were pre-added. The NaOAc diluted compound plate was spun down to pellet precipitant and 20 μL/well was transferred to a corresponding flat-bottom plate to which 30 μL of ice-cold enzyme-substrate mixture (2.5 μL MBP-C125 substrate, 0.03 μL enzyme and 24.5 ice cold 0.09% TX100 per 30 μl) was added. The compound concentration in the final enzyme reaction was thus 50 times less than the starting concentration. The final reaction mixture of 200 μM compound for the highest curve point was in 5% DMSO, 20 mM NaAc, 0.06% TX100, at pH 4.5. The enzyme reaction was started by warming the plates to 37° C. After 90 minutes at 37° C., 200 μL/well cold specimen diluent was added to stop the reaction and 20 μL/well was transferred to a corresponding α-MBP coated ELISA plate, containing 80 μL/well specimen diluent. This reaction was incubated overnight at 4° C. and the ELISA was developed the next day using a 2 hr. incubation with α-192SW followed by Streptavidin-AP conjugate and flourescent substrate. The signal was read on a fluorescent plate reader.

Methods for Treating Alzheimer's Disease and Other Diseases Characterized by Deposition of Aβ Peptide.

This invention also relates to a method of treatment for patients suffering from disorders or diseases which can be attributed to Aβ plaque formation as previously described and, more specifically, a method of treatment involving the administration of the β-secretase inhibitors of formula 1 as the active constituents.

Accordingly, the compounds of formula 1 can be used among other things in the treatment Alzheimer's disease, and in diseases and indications resulting from the over-expression of Aβ-peptide such as found in certain genetic defect diseases such as plaque formation associated with Trisomy 21 (Down's Syndrome) and Hereditary Cerebral Hemorrhage with Amyloidosis of the Dutch-Type (HCHWA-D).

As mentioned above, compounds of formula 1 are useful in medicine since they are active as inhibitors of β-secretase. Accordingly another aspect, this invention concerns:

a method of management (by which is meant treatment or prophylaxis) of disease or conditions mediated by β-secretase in mammals, in particular in humans, which method comprises administering to the mammal an effective, amount of a compound of formula 1 above, or a pharmaceutically acceptable salt or ester thereof; and a compound of formula (I) for use in human or veterinary medicine, particularly in the management (by which is meant treatment or prophylaxis) of diseases or conditions mediated by β-secretase; and the use of a compound of formula (I) in the preparation of a composition for the management (by which is meant treatment or prophylaxis) of diseases or conditions mediated by β-secretase.

The disease or conditions referred to above include Alzheimer's disease, plaque formation associated with Trisomy 21 (Down's Syndrome) and Hereditary Cerebral Hemorrhage with Amyloidosis of the Dutch-Type (HCHWA-D).

For the treatment of diseases characterized by the over-production and deposition of Aβ-ppeptide, the compunds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. The compounds may be administered in an amount from about 0.1 mg/kg/day to about 500 mg/kg/day. Preferred amounts for daily administration are from about 1 mg/kg to about 50 mg/kg. It will be understood however, that the amount of the compound actually administered will be determined by a physician in the light of the relevant circumstances, including the condition to be treated, the chosen route of administration, the actual compound administered, the age, weight and response of the individual patient, the severity of the patient's symptoms, and the like.

Formulation of Pharmaceutical Compositions

Compositions are provided that contain therapeutically effective amounts of the compounds of formula 1. The compounds are preferably formulated into suitable pharmaceutical preparations such as tablets, capsules or elixirs, for oral administration or in sterile solutions or suspensions for parenteral administration. Typically the compounds described above are formulated into pharmaceutical compositions using techniques and procedures well known in the art.

About 1 to 500 mg of a compound or mixture of compounds for Formula 1 or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

To prepare compositions, one or more compounds of formula 1 are mixed with a suitable pharmaceutically acceptable carrier. Upon mixing or addition of the compound(s), the resulting mixture may be a solution, suspension, emulsion or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action or have other action. The compounds may be formulated as the sole pharmaceutically active ingredient in the composition or may be combined with other active ingredients.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as Tween®, or dissolution in aqueous sodium bicarbonate. Derivatives of the compounds, such as salts of the compounds or prodrugs of the compounds may also be used in formulating effective pharmaceutical compositions.

The concentrations of the compounds are effective for delivery of an amount, upon administration, that ameliorates the symptoms of the disorder for which the compounds are administered. Typically, the compositions are formulated for single dosage administration.

The compounds of formula 1 may be prepared with carriers that protect them against rapid elimination from the body, such as time release formulations or coatings. Such carriers include controlled release formulations, such as, but not limited to, microencapsulated delivery systems, The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compositions can be enclosed in ampoules, disposable syringes or multiple or single dose vials made of glass, plastic or other suitable material. Such enclosed compositions can be provided in kits.

The concentration of active compound in the drug composition will depend on absorption, inactivation and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as, but not limited to, gum tragacanth, acacia, corn starch or gelatin; an excipient such as microcrystalline cellulose, starch and lactose, a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action.

Solutions or suspensions used for parenteral, intradermal, subcutaneous, or topical application can include any of the following components: a sterile diluent, such as water for injection, saline solution, fixed oil, a naturally occurring vegetable oil like sesame oil, coconut oil, peanut oil, cottonseed oil, etc. or a synthetic fatty vehicle like ethyl oleate or the like, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or multiple dose vials made of glass, plastic or other suitable material. Buffers, preservatives, antioxidants and the like can be incorporated as required.

If administered intravenously, suitable carriers include physiological saline or phosphate buffered saline (PBS), and solutions containing thickening and solubilizing agents, such as glucose, polyethylene glycol, and polypropyleneglycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such

We claim:
1. A compound of formula 1

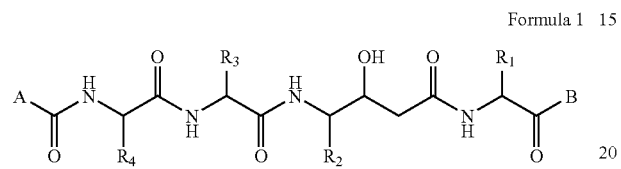

Formula 1 wherein
A is a straight or branched chain alkanoxy or alkenoxy of 1 to 5 carbon atoms, aryl, arylalkyl, the aryl being optionally substituted with 1 to 2 carbon atoms or halogen, adamantyloxy, or 4-aminobutanoic acid;
B is selected from the group consisting of hydroxy,

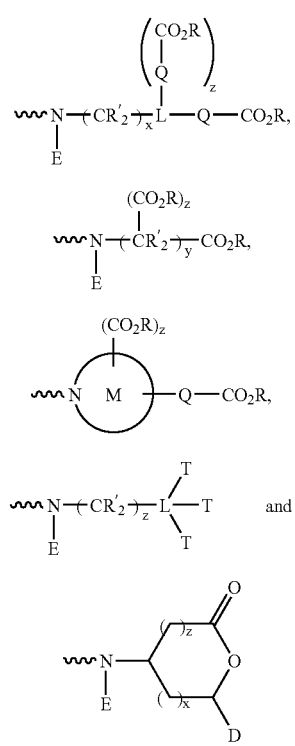

wherein a dithered line represents a point of attachment at B of formula 1;
D is H or an oxo group;
L is a 5 or 6 membered saturated, unsaturated or aromatic heterocycle having from 1 to 3 heteroatoms chosen from nitrogen, oxygen and sulfur, or a saturated, unsaturated or aromatic carbocycle of 3 to 6 carbon atoms, any group represented by L having optional substitution with R', OR', or halogen;
Q is a bond, or is a straight chain linking group of 1 to 3 non-hydrogen atoms chosen from the group consisting of —$CH_2$—, —O—, and —NH— wherein O and N may not be adjacent;
ring M is a stable 5 to 7-membered saturated, unsaturated or aromatic heterocycle having up to 2 additional N atoms and optionally having 1 to 2 atoms of O and S,
T is independently selected from the group consisting of H, OH, $NO_2$, $C(O)N(R)_2$, F, $C_1$–$C_3$ alkoxy, hydroxymethyl and $CF_3$, wherein at least one T is other than H;
x is an integer of 1 to 3,
y is an integer of 1 to 6,
z is 0 (zero), 1 or 2,
R' is independently H, —OH, $C_1$–$C_2$ alkyl or phenyl,
R is independently H, $C_1$–$C_4$ alkyl, or phenyl, and E is H, or $C_1$–$C_2$ alkyl;
$R_1$ is $C_1$–$C_5$ alkyl;
$R_2$ is 2-propyl, 1-(2-methylpropyl)- or phenyl optionally substituted with R', OR' or halogen;
$R_3$ is phenyl, $C_1$–$C_5$ alkyl, or 1-(2-methylthio-)ethyl-;
$R_4$ is 2-propyl, 2-butyl or 2-methylpropyl;
and stereoisomers, hydrates and pharmaceutically acceptable salts and esters thereof.

2. The compound of claim 1 wherein B is the group (i) wherein L is cyclohexane, x=0, z=0 or 1, Q is —$CH_2$— or a bond and E and R' are both H and R is H or $C_1$–$C_5$ alkyl.

3. The compound of claim 2 wherein B is selected from the group consisting of 3,5-dicarboxycyclohexylamine, 3,4-dicarboxycyclohexylamine and 2,4-dicarboxycyclohexylamine and 2,5-dicarboxycyclohexylamine.

4. The compound of claim 1 wherein B is the group (i) wherein L is phenyl, x=1, z=0, Q is selected from a bond, —$CH_2$— and —O—$CH_2$—, R' is H and E is H or $CH_3$, and R is H or $C_1$–$C_5$ alkyl.

5. The compound of claim 4 wherein B is selected from the group consisting of 4-aminomethylbenzoic acid; 4-methylaminomethylbenzoic acid; 1-amino-1-(4-carboxyphenyl)ethane; 2-aminomethylbenzoxyacetic acid; 2-aminobenzoic acid and 4-aminobenzoic acid.

6. The compound of claim 1 wherein B is the group (ii) wherein y is from 2 to 6 inclusive, z=0 or 1 and R' and E are both H and R is H or $C_{1-5}$ alkyl.

7. The compound of claim 6 wherein B is selected from the group consisting of 4-aminobutanoic acid-3-aminopropanoic acid and glutamic acid.

8. The compound of claim 1 wherein B is the group (v) wherein x=1 and z=0.

9. The compound of claim 8 wherein B is selected from the group consisting of 3-aminofuran-2-one and 2-aminopentanedioic acid anhydride.

10. The compound of claim 1 wherein B is the group (v) wherein ring M is a 6-membered heterocycle having 1 to 2 atoms of N, z=0, Q is a bond or $CH_2$ and R is H or $C_1$–$C_5$ alkyl.

11. The compound of claim 10 wherein B is selected from the group consisting of 4-piperidineacetic acid and piperazine-4-carboxylic acid.

12. The compound of claim 1 wherein B is the group (iv) wherein L is phenyl and T is selected from the group consisting of H, OH, F, $NO_2$, $C(O)NH_2$, $C_1$–$C_2$ alkoxy and hydroxymethyl.

13. The compound of claim 12 wherein B is selected from the group consisting of 1-amino-2-(3-nitro-4-hydroxyphenyl)ethane, 4-fluorobenzenamine, and aminomethylbenzene-4-carboxamide.

14. The compound of claim 1 wherein B is selected from 2-aminomethylthiazole-5-carboxylic acid and phenylglycine.

15. The compound of claim 1 wherein B is selected from 3,5-dimethoxycyclohexylamine, 3,5-dihydroxymethylcyclohexylamine and 3,4,5-trimethoxycyclohexylamine.

16. The compound of claim 1 wherein $R_1$ is 2-propyl and $R_2$ is chosen from the group consisting of 2-methylpropyl and benzyl.

17. The compound of claim 16 wherein B is the group (i) wherein L is cyclohexane, x=0, z=0 or 1, Q is —$CH_2$— or a bond and E and R' are both H and R is H or $C_1$–$C_5$ alkyl.

18. The compound of claim 17 wherein B is selected from the group consisting of 3,5-dicarboxycyclohexylamine, 3,4-dicarboxycyclohexylamine and 2,4-dicarboxycyclohexylamine and 2,5-dicarboxycyclohexylamine.

19. The compound of claim 16 wherein B is selected from the group consisting of 4-aminomethylbenzoic acid, 4-methylaminomethylbenzoic acid1-amino-1-(4-carboxyphenyl)ethane, 2-aminomethylbenzoxyacetic acid, 2-aminobenzoic acid and 4-aminobenzoic acid.

20. The compound of claim 16 wherein B is selected from the group consisting of 4-aminobutanoic acid-3-aminoporpanoic acid and glutamic acid.

21. The compound of claim 16 wherein B is selected from the group consisting of 3-aminofuran-2-one and 2-aminopentanedioic acid anhydride.

22. The compound of claim 16 wherein B is selected from the group consisting of 4-piperidineacetic acid and piperazine-4-carboxylic acid.

23. The compound of claim 16 wherein B is selected from the group consisting of 1-amino-2-(3-nitro-4-hydroxyphenyl)ethane, 4-fluorobenzenamine, and aminomethylbenzene-4-carboxamide.

24. The compound of claim 16 wherein B is selected from 2-aminomethylthiazole-5-carboxylic acid and phenylglycine.

25. The compound of claim 16 wherein B is selected from 3,5-dimethoxycyclohexylamine, 3,5-dihydroxymethylcyclohexylamine and 3,4,5-trimethoxycyclohexylamine.

26. The compound of claim 1 wherein $R_3$ is selected from the group consisting of phenyl and 2-methylthioethyl and R4 is 2-propyl.

27. The compound of claim 16 wherein $R_3$ is selected from the group consisting of phenyl and 2-methylthioethyl and R4 is 2-propyl.

28. The compound of claim 17 wherein $R_3$ is selected from the group consisting of phenyl and 2-methylthioethyl and R4 is 2-propyl.

29. The compound of claim 18 wherein $R_3$ is selected from the group consisting of phenyl and 2-methylthioethyl and R4 is 2-propyl.

30. The compound of claim 19 wherein $R_3$ is selected from the group consisting of phenyl and 2-methylthioethyl and R4 is 2-propyl.

31. The compound of claim 20 wherein $R_3$ is selected from the group consisting of phenyl and 2-methylthioethyl and R4 is 2-propyl.

32. The compound of claim 21 wherein $R_3$ is selected from the group consisting of phenyl and 2-methylthioethyl and R4 is 2-propyl.

33. The compound of claim 22 wherein $R_3$ is selected from the group consisting of phenyl and 2-methylthioethyl and R4 is 2-propyl.

34. The compound of claim 23 wherein $R_3$ is selected from the group consisting of phenyl and 2-methylthioethyl and R4 is 2-propyl.

35. The compound of claim 24 wherein $R_3$ is selected from the group consisting of phenyl and 2-methylthioethyl and R4 is 2-propyl.

36. The compound of claim 25 wherein $R_3$ is selected from the group consisting of phenyl and 2-methylthioethyl and R4 is 2-propyl.

37. The compound of claim 26 wherein $R_3$ is selected from the group consisting of phenyl and 2-methylthioethyl and R4 is 2-propyl.

38. A method of slowing the progression of a disease state characterized by deposition of Aβ peptide in a mammal comprising administering to a mammal in need thereof an effective amount of a compound of Formula 1

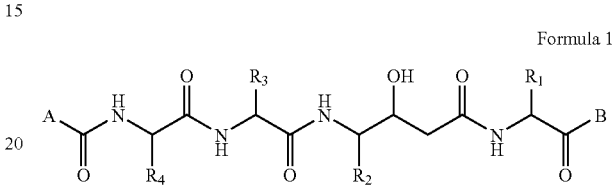

Formula 1 wherein

A is a straight or branched chain alkanoxy or alkenoxy of 1 to 5 carbon atoms, aryl, arylalkyl, the aryl being optionally substituted with 1 to 2 carbon atoms or halogen, adamantyloxy, or 4-aminobutanoic acid;

B is selected from the group consisting of hydroxy,

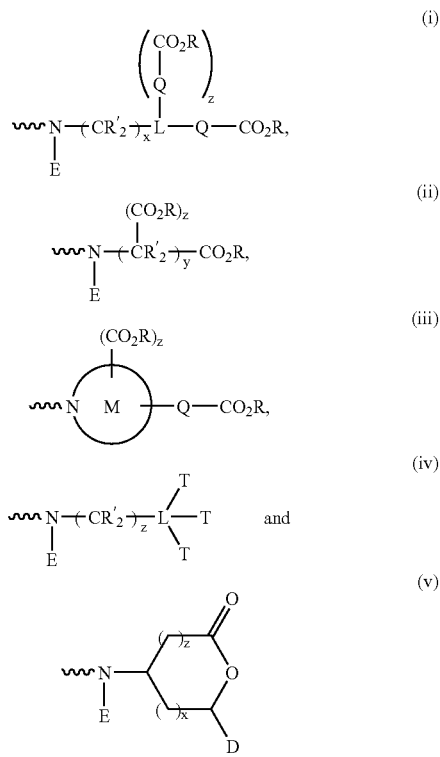

wherein a dithered line represents a point of attachment at B of formula 1;

D is H or an oxo group;

L is a 5 or 6 membered saturated, unsaturated or aromatic heterocycle having from 1 to 3 heteroatoms chosen from nitrogen, oxygen and sulfur, or a saturated, unsaturated or aromatic carbocycle of 3 to 6 carbon atoms, any group represented by L having optional substitution with R', OR', or halogen;

Q is a bond, or is a straight chain linking group of 1 to 3 non-hydrogen atoms chosen from the group consisting of —$CH_2$—, —O—, and —NH— wherein O and N may not be adjacent;

ring M is a stable 5 to 7-membered saturated, unsaturated or aromatic heterocycle having up to 2 additional N atoms and optionally having 1 to 2 atoms of O and S, T is independently selected from the group consisting of H, OH, $NO_2$, $C(O)N(R)_2$, F, $C_1$–$C_3$ alkoxy, hydroxymethyl and $CF_3$, wherein at least one T is other than H;

x is an integer of 1 to 3, y is an integer of 1 to 6, z is 0 (zero), 1 or 2,

R' is independently H, —OH, $C_1$–$C_2$ alkyl or phenyl,

R is independently H, $C_1$–$C_4$ alkyl, or phenyl, and E is H, or $C_1$–$C_2$ alkyl;

$R_1$ is $C_1$–$C_5$ alkyl;

$R_2$ is 2-propyl, 1-(2-methylpropyl)- or phenyl optionally substituted with R', OR' or halogen;

$R_3$ is phenyl, $C_1$–$C_5$ alkyl, or 1-(2-methylthio-)ethyl-;

$R_4$ is 2-propyl, 2-butyl or 2-methylpropyl;

and stereoisomers, hydrates and pharmaceutically acceptable salts and esters thereof.

39. The method of claim 38 wherein B is the group (i) wherein L is cyclohexane, x=0, z=0 or 1, Q is —$CH_2$— or a bond and E and R' are both H and R is H or $C_1$–$C_5$ alkyl.

40. The method of claim 39 wherein B is selected from the group consisting of 3,5-dicarboxycyclohexylamine, 3,4-dicarboxycyclohexylamine and 2,4-dicarboxycyclohexylamine and 2,5-dicarboxycyclohexylamine.

41. The method of claim 38 wherein B is the group (i) wherein L is phenyl, x=1, z=0, Q is selected from a bond, —$CH_2$— and —O—$CH_2$—, R' is H and E is H or $CH_3$, and R is H or $C_1$–$C_5$ alkyl.

42. The method of claim 41 wherein B is selected from the group consisting of 4-aminomethylbenzoic acid; 4-methylaminomethylbenzoic acid; 1-amino-1-(4-carboxyphenyl) ethane; 2-aminomethylbenzoxyacetic acid; 2-aminobenzoic acid and 4-aminobenzoic acid.

43. The method of claim 38 wherein B is the group (ii) wherein y is from 2 to 6 inclusive, z=0 or 1 and R' and E are both H and R is H or $C_{1-5}$ alkyl.

44. The method of claim 43 wherein B is selected from the group consisting of 4-aminobutanoic acid-3-aminopropanoic acid and glutamic acid.

45. The method of claim 38 wherein B is the group (v) wherein x=1 and z=0.

46. The method of claim 45 wherein B is selected from the group consisting of 3-aminofuran-2-one and 2-aminopentanedioic acid anhydride.

47. The method of claim 38 wherein B is the group (v) wherein ring M is a 6-membered heterocycle having 1 to 2 atoms of N, z=0, Q is a bond or $CH_2$ and R is H or $C_1$–$C_5$ alkyl.

48. The method of claim 47 wherein B is selected from the group consisting of 4-piperidineacetic acid and piperazine-4-carboxylic acid.

49. The method of claim 38 wherein B is the group (iv) wherein L is phenyl and T is selected from the group consisting of H, OH, F, $NO_2$, $C(O)NH_2$, $C_1$–$C_2$ alkoxy and hydroxymethyl.

50. The method of claim 49 wherein B is selected from the group consisting of 1-amino-2-(3-nitro-4-hydroxyphenyl) ethane, 4-fluorobenzenamine, and aminomethylbenzene-4-carboxamide.

51. The method of claim 38 wherein B is selected from 2-aminomethylthiazole-5-carboxylic acid and phenylglycine.

52. The method of claim 38 wherein B is selected from 3,5-dimethoxycyclohexylamine, 3,5-dihydroxymethylcyclohexylamine and 3,4,5-trimethoxycyclohexylamine.

53. The method of claim 38 wherein $R_1$ is 2-propyl and $R_2$ is chosen from the group consisting of 2-methylpropyl and benzyl.

54. The method of claim 53 wherein B is the group (i) wherein L is cyclohexane, x=0, z=0 or 1, Q is —$CH_2$— or a bond and E and R' are both H and R is H or $C_1$–$C_5$ alkyl.

55. The method of claim 54 wherein B is selected from the group consisting of 3,5-dicarboxycyclohexylamine, 3,4-dicarboxycyclohexylamine and 2,4-dicarboxycyclohexylamine and 2,5-dicarboxycyclohexylamine.

56. The method of claim 53 wherein B is selected from the group consisting of 4-aminomethylbenzoic acid, 4-methylaminomethylbenzoic acid1-amino-1-(4-carboxyphenyl) ethane, 2-aminomethylbenzoxyacetic acid, 2-aminobenzoic acid and 4-aminobenzoic acid.

57. The method of claim 53 wherein B is selected from the group consisting of 4-aminobutanoic acid-3-aminoporpanoic acid and glutamic acid.

58. The method of claim 53 wherein B is selected from the group consisting of 3-aminofuran-2-one and 2-aminopentanedioic acid anhydride.

59. The method of claim 53 wherein B is selected from the group consisting of 4-piperidineacetic acid and piperazine-4-carboxylic acid.

60. The method of claim 53 wherein B is selected from the group consisting of 1-amino-2-(3-nitro-4-hydroxyphenyl) ethane, 4-fluorobenzenamine, and aminomethylbenzene-4-carboxamide.

61. The method of claim 53 wherein B is selected from 2-aminomethylthiazole-5-carboxylic acid and phenylglycine.

62. The method of claim 53 wherein B is selected from 3,5-dimethoxycyclohexylamine, 3,5-dihydroxymethylcyclohexylamine and 3,4,5-trimethoxycyclohexylamine.

63. The method of claim 38 wherein $R_3$ is selected from the group consisting of phenyl and 2-methylthioethyl and R4 is 2-propyl.

64. The method of claim 43 wherein $R_3$ is selected from the group consisting of phenyl and 2-methylthioethyl and R4 is 2-propyl.

65. The method of claim 44 wherein $R_3$ is selected from the group consisting of phenyl and 2-methylthioethyl and R4 is 2-propyl.

66. The method of claim 45 wherein $R_3$ is selected from the group consisting of phenyl and 2-methylthioethyl and R4 is 2-propyl.

67. The method of claim 46 wherein $R_3$ is selected from the group consisting of phenyl and 2-methylthioethyl and R4 is 2-propyl.

68. The method of claim 47 wherein $R_3$ is selected from the group consisting of phenyl and 2-methylthioethyl and R4 is 2-propyl.

69. The method of claim 48 wherein $R_3$ is selected from the group consisting of phenyl and 2-methylthioethyl and R4 is 2-propyl.

70. The method of claim 49 wherein $R_3$ is selected from the group consisting of phenyl and 2-methylthioethyl and R4 is 2-propyl.

71. The method of claim 50 wherein $R_3$ is selected from the group consisting of phenyl and 2-methylthioethyl and R4 is 2-propyl.

72. The method of claim 51 wherein $R_3$ is selected from the group consisting of phenyl and 2-methylthioethyl and R4 is 2-propyl.

73. The method of claim 52 wherein $R_3$ is selected from the group consisting of phenyl and 2-methylthioethyl and R4 is 2-propyl.

74. The method of claim 53 wherein $R_3$ is selected from the group consisting of phenyl and 2-methylthioethyl and R4 is 2-propyl.

75. A pharmaceutical composition comprising a compound of formula 1

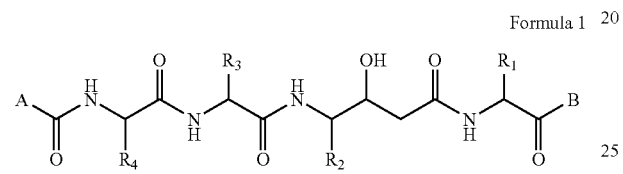

Formula 1 wherein

A is a straight or branched chain alkanoxy or alkenoxy of 1 to 5 carbon atoms, aryl, arylalkyl, the aryl being optionally substituted with 1 to 2 carbon atoms or halogen, adamantyloxy, or 4-aminobutanoic acid;

B is selected from the group consisting of hydroxy,

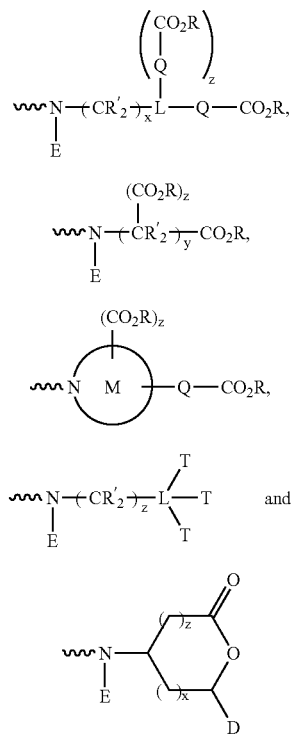

wherein a dithered line represents a point of attachment at B of formula 1;

D is H or an oxo group;

L is a 5 or 6 membered saturated, unsaturated or aromatic heterocycle having from 1 to 3 heteroatoms chosen from nitrogen, oxygen and sulfur, or a saturated, unsaturated or aromatic carbocycle of 3 to 6 carbon atoms, any group represented by L having optional substitution with R', OR', or halogen;

Q is a bond, or is a straight chain linking group of 1 to 3 non-hydrogen atoms chosen from the group consisting of —$CH_2$—, —O—, and —NH— wherein O and N may not be adjacent;

ring M is a stable 5 to 7-membered saturated, unsaturated or aromatic heterocycle having up to 2 additional N atoms and optionally having 1 to 2 atoms of O and S, T is independently selected from the group consisting of H, OH, $NO_2$, $C(O)N(R)_2$, F, $C_1$–$C_3$ alkoxy, hydroxymethyl and $CF_3$, wherein at least one T is other than H;

x is an integer of 1 to 3, y is an integer of 1 to 6, z is 0 (zero), 1 or 2,

R' is independently H, —OH, $C_1$–$C_2$ alkyl or phenyl,

R is independently H, $C_1$–$C_4$ alkyl, or phenyl, and E is H, or $C_1$–$C_2$ alkyl;

$R_1$ is $C_1$–$C_5$ alkyl;

$R_2$ is 2-propyl, 1-(2-methylpropyl)- or phenyl optionally substituted with R', OR' or halogen;

$R_3$ is phenyl, $C_1$–$C_5$ alkyl, or 1-(2-methylthio-)ethyl-;

$R_4$ is 2-propyl, 2-butyl or 2-methylpropyl;

and hydrates, pharmaceutically acceptable salts and esters thereof and a pharmaceutically acceptable diluent.

76. The composition of claim 75 wherein B is the group (i) wherein L is cyclohexane, x=0, z=0 or 1, Q is —$CH_2$— or a bond and E and R' are both H and R is H or $C_1$–$C_5$ alkyl.

77. The composition of claim 76 wherein B is selected from the group consisting of 3,5-dicarboxycyclohexylamine, 3,4-dicarboxycyclohexylamine and 2,4-dicarboxycyclohexylamine and 2,5-dicarboxycyclohexylamine.

78. The composition of claim 75 wherein B is the group (i) wherein L is phenyl, x=1, z=0, Q is selected from a bond, —$CH_2$— and —O—$CH_2$—, R' is H and E is H or $CH_3$, and R is H or $C_1$–$C_5$ alkyl.

79. The composition of claim 78 wherein B is selected from the group consisting of 4-aminomethylbenzoic acid; 4-methylaminomethylbenzoic acid; 1-amino-1-(4-carboxyphenyl)ethane; 2-aminomethylbenzoxyacetic acid; 2-aminobenzoic acid and 4-aminobenzoic acid.

80. The composition of claim 75 wherein B is the group (ii) wherein y is from 2 to 6 inclusive, z=0 or 1 and R' and E are both H and R is H or $C_{1-5}$ alkyl.

81. The composition of claim 80 wherein B is selected from the group consisting of 4-aminobutanoic acid-3-aminopropanoic acid and glutamic acid.

82. The composition of claim 75 wherein B is the group (v) wherein x=1 and z=0.

83. The composition of claim 82 wherein B is selected from the group consisting of 3-aminofuran-2-one and 2-aminopentanedioic acid anhydride.

84. The composition of claim 75 wherein B is the group (v) wherein ring M is a 6-membered heterocycle having 1 to 2 atoms of N, z=0, Q is a bond or $CH_2$ and R is H or $C_1$–$C_5$ alkyl.

85. The composition of claim 75 wherein B is selected from the group consisting of 4-piperidineacetic acid and piperazine-4-carboxylic acid.

86. The composition of claim 75 wherein B is the group (iv) wherein L is phenyl and T is selected from the group consisting of H, OH, F, $NO_2$, $C(O)NH_2$, $C_1$–$C_2$ alkoxy and hydroxymethyl.

87. The composition of claim 86 wherein B is selected from the group consisting of 1-amino-2-(3-nitro-4-hydroxyphenyl)ethane, 4-fluorobenzenamine, and aminomethylbenzene-4-carboxamide.

88. The composition of claim 75 wherein B is selected from 2-aminomethylthiazole-5-carboxylic acid and phenylglycine.

89. The composition of claim 75 wherein B is selected from 3,5-dimethoxycyclohexylamine, 3,5-dihydroxymethylcyclohexylamine and 3,4,5-trimethoxycyclohexylamine.

90. The composition of claim 75 wherein $R_1$ is 2-propyl and $R_2$ is chosen from the group consisting of 2-methylpropyl and benzyl.

91. The composition of claim 90 wherein B is the group (i) wherein L is cyclohexane, x=0, z=0 or 1, Q is —$CH_2$— or a bond and E and R' are both H and R is H or $C_1$–$C_5$ alkyl.

92. The composition of claim 91 wherein B is selected from the group consisting of 3,5-dicarboxycyclohexylamine, 3,4-dicarboxycyclohexylamine and 2,4-dicarboxycyclohexylamine and 2,5-dicarboxycyclohexylamine.

93. The composition of claim 90 wherein B is selected from the group consisting of 4-aminomethylbenzoic acid, 4-methylaminomethylbenzoic acid 1-amino-1-(4-carboxyphenyl)ethane, 2-aminomethylbenzoxyacetic acid, 2-aminobenzoic acid and 4-aminobenzoic acid.

94. The composition of claim 90 wherein B is selected from the group consisting of 4-aminobutanoic acid-3-aminoporpanoic acid and glutamic acid.

95. The composition of claim 90 wherein B is selected from the group consisting of 3-aminofuran-2-one and 2-aminopentanedioic acid anhydride.

96. The composition of claim 90 wherein B is selected from the group consisting of 4-piperidineacetic acid and piperazine-4-carboxylic acid.

97. The composition of claim 90 wherein B is selected from the group consisting of 1-amino-2-(3-nitro-4-hydroxyphenyl)ethane, 4-fluorobenzenamine, and aminomethylbenzene-4-carboxamide.

98. The composition of claim 90 wherein B is selected from 2-aminomethylthiazole-5-carboxylic acid and phenylglycine.

99. The composition of claim 90 wherein B is selected from 3,5-dimethoxycyclohexylamine, 3,5-dihydroxymethylcyclohexylamine and 3,4,5-trimethoxycyclohexylamine.

100. The composition of claim 75 wherein $R_3$ is selected from the group consisting of phenyl and 2-methylthioethyl and R4 is 2-propyl.

101. The composition of claim 90 wherein $R_3$ is selected from the group consisting of phenyl and 2-methylthioethyl and R4 is 2-propyl.

102. The composition of claim 91 wherein $R_3$ is selected from the group consisting of phenyl and 2-methylthio ethyl and R4 is 2-propyl.

103. The composition of claim 92 wherein $R_3$ is selected from the group consisting of phenyl and 2-methylthioethyl and R4 is 2-propyl.

104. The composition of claim 93 wherein $R_3$ is selected from the group consisting of phenyl and 2-methylthioethyl and R4 is 2-propyl.

105. The composition of claim 94 wherein $R_3$ is selected from the group consisting of phenyl and 2-methylthioethyl and R4 is 2-propyl.

106. The composition of claim 95 wherein $R_3$ is selected from the group consisting of phenyl and 2-methylthioethyl and R4 is 2-propyl.

107. The composition of claim 96 wherein $R_3$ is selected from the group consisting of phenyl and 2-methylthioethyl and R4 is 2-propyl.

108. The composition of claim 97 wherein $R_3$ is selected from the group consisting of phenyl and 2-methylthioethyl and R4 is 2-propyl.

109. The composition of claim 98 wherein $R_3$ is selected from the group consisting of phenyl and 2-methylthioethyl and R4 is 2-propyl.

110. The composition of claim 99 wherein $R_3$ is selected from the group consisting of phenyl and 2-methylthioethyl and R4 is 2-propyl.

111. The composition of claim 100 wherein $R_3$ is selected from the group consisting of phenyl and 2-methylthioethyl and R4 is 2-propyl.

* * * * *